United States Patent [19]

Chiang et al.

[11] Patent Number: 5,607,936
[45] Date of Patent: Mar. 4, 1997

[54] SUBSTITUTED ARYL PIPERAZINES AS NEUROKININ ANTAGONISTS

[75] Inventors: Yuan-Ching P. Chiang, Scotch Plains; Paul E. Finke, Milltown; Malcolm Maccoss, Freehold; Laura C. Meurer, Scotch Plains; Daniel J. Miller, Edison; Sander G. Mills, Woodbridge; Albert J. Robichaud, Stirling; Shrenik K. Shah, Metuchen, all of N.J.

[73] Assignee: Merck & Co., Inc., Rahway, N.J.

[21] Appl. No.: 316,013

[22] Filed: Sep. 30, 1994

[51] Int. Cl.⁶ .................. C07D 403/10; A61K 31/495
[52] U.S. Cl. .................. 514/255; 544/365; 544/366; 544/370; 544/393; 544/395
[58] Field of Search .................. 546/393, 370, 546/366, 395, 365; 514/255

[56] References Cited

U.S. PATENT DOCUMENTS

| 3,301,857 | 1/1967 | Berger et al. | 514/278 |
|---|---|---|---|
| 4,233,307 | 11/1980 | Ono et al. | 514/278 |
| 4,420,485 | 12/1983 | Davis et al. | 514/278 |
| 4,515,793 | 5/1985 | Werbel | 514/252 |
| 4,605,655 | 8/1986 | Yevuich | 514/252 |
| 5,091,387 | 2/1992 | Evans et al. | |

FOREIGN PATENT DOCUMENTS

| 2067877 | 11/1992 | Canada. |
|---|---|---|
| 0360390 | 3/1990 | European Pat. Off. . |
| 0428434A2 | 5/1991 | European Pat. Off. . |
| 0431943A2 | 6/1991 | European Pat. Off. . |
| 0450761 | 10/1991 | European Pat. Off. . |
| 0474561A1 | 3/1992 | European Pat. Off. . |
| 0512901A1 | 11/1992 | European Pat. Off. . |
| 0518805 | 12/1992 | European Pat. Off. . |
| 0559538 | 9/1993 | European Pat. Off. . |

OTHER PUBLICATIONS

Misztal, et al, Chem, Ab., vol. 110, No. 21, 193172d (1989).
Ong, et al, Journ. of Heterocyclic Chem., vol. 18, pp. 815–820 (1981).
Hoechst, Chem. Ab., vol. 90, No. 17, 137699n (1979).
C. Advenier, et al., Biochem and Biophys Res. Comm vol. 184, No. 3, pp. 1418–1424 (May 15, 1992).
X. Emonds–Alt, et al., Life Sciences, vol. 50, No. 15, pp. PL–101 PL–106 (1992).
Y. Hirayama, et al., J. Pharmacol (1993) 108, 844–851, Y. Hirayama, et al.
C. A. Maggi, et al., J. Auton. Pharmacol. 13, pp. 23–93 (1993).

*Primary Examiner*—Robert Gerstl
*Attorney, Agent, or Firm*—Curtis C. Panzer; David L. Rose

[57] ABSTRACT

Disclosed are substituted aryl piperazines of Formula I

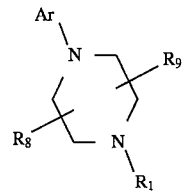

are tachykinin receptor antagonists useful in the treatment of inflammatory diseases, pain or migraine, asthma and emesis. In particular compounds of Formula I are shown to be neurokinin antagonists.

12 Claims, No Drawings

5,607,936

SUBSTITUTED ARYL PIPERAZINES AS NEUROKININ ANTAGONISTS

BACKGROUND OF THE INVENTION

The invention disclosed herein is directed to certain substituted aryl piperazines useful as tachykinin receptor antagonists. In particular, the compounds disclosed herein are neurokinin receptor antagonists.

The tachykinins, substance P (SP), neurokinin A (NKA) and neurokinin B (NKB), are structurally similar members of a family of neuropeptides. Each of these is an agonist of the receptor types, neurokinin-1 receptor (NK-1), neuorokinin-2 receptor (NK-2) and neuorokinin-3 receptor (NK-3), which are so defined according to their relative abilities to bind tachykinins with high affinity and to be activated by the natural agonists SP, NKA and NKB respectively.

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85–141). The NK1 and NK2 receptor subtypes are implicated in synaptic transmission (Laneuville et al., *Life Sci.*, 42: 1295–1305 (1988)).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, 199, 1359 (1978); P. Oehme et al., *Science*, 208, 305 (1980)) and plays a role in sensory transmission and pain perception (T. M. Jessell, *Advan. Biochem. Psychopharmacol.* 28, 189 (1981)). In particular, substance P has been shown to be involved in the transmission of pain in migraine (see B. E. B. Sandberg et al., *Journal of Medicinal Chemistry*, 25, 1009 (1982)), and in arthritis (Levine et al., *Science*, (1984) 226 547–549).

In the airways, it has been indicated that NK1 receptors are associated with microvascular leakage and mucus secretion, while NK2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al., *Life Sci.*, 49, 1941–1953 (1991); Advenier, et al., *Biochem. Biophys. Res. Comm.*, 184(3), 1418–1424 (1992)).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (Barnes P. J., *Lancet*, pp 242–44 (1986); Rogers D. R., Aursudkij B., Barnes P. J., *Euro. J. Pharmacol*, 174, 283–86 (1989)).

Inhalation of bradykinin causes bronchoconstriction in asthmatic patients but not in normal subjects. (Fuller R. W., Dixon C. M. S., Cuss F. M. C., Barnes P. J., *Am Rev Respir Dis*, 135, 176–80 (1987)). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes bronchoconstriction in dogs. (Kaufman M. P., Coleridge H. M., Coleridge J. C. G., Baker D. G., *J. Appl. Physio.*, 48, 511–17 (1980)). In guinea-pig airways, bradykinin causes a bronchoconstrictor response by way of cholinergic and sensory-nerve-mediated mechanisms. (Ichinoe M., Belvisi M. G., Barnes P. J., *J. Pharmacol. Exp. Ther.*, 253, 594–99 (1990). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchoconstriction in asthmatic patients. (Ichinoe, M. et al., *Lancet, vol.* 340, pp 1248–1251 (1992)).

The tachykinins have also been implicated in gastrointestinal (GI) disorders and diseases of the GI tract, such as inflammatory bowel disease, ulcerative colitis and Crohn's disease, etc. (see Mantyh et al., *Neuroscience*, 25 (3), 817–37 (1988) and D. Regoli in *Trends in Cluster Headache* Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in *The Lancet*, 11 Nov. 1989 and Gronblad et al., "Neuropeptides in Synovium of Patients with Rheumatoid Arthritis and Osteoarthritis" in *J. Rheumatol.* (1988) 15(12) 1807–10). Therefore, substance P is believed to be involved in the inflammatory response in diseases such as rheumatoid arthritis and osteoarthritis (O'Byrne et al., in *Arthritis and Rheumatism* (1990) 33 1023–8). Other disease areas where tachykinin antagonists are believed to be useful are allergic conditions (Hamelet et al., *Can. J. Pharmacol. Physiol.* (1988) 66 1361–7), immunoregulation (Lotz et al., *Science* (1988) 241 1218–21, Kimball et al., *J. Immunol.* (1988) 141 (10) 3564–9 and A. Perianin, et al., *Biochem. Biophys. Res. Commun.* 161, 520 (1989)) vasodilation, bronchospasm, reflex or neuronal control of the viscera (Mantyh et al., *PNAS* (1988) 85 3235–9) and, possibly by arresting or slowing β-amyloid-mediated neurodegenerative changes (Yankner et al., *Science*, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis (J. Luber-Narod et al., poster presented at C.I.N.P. XVIIIth Congress, 28th June-2nd July, 1992). Antagonists selective for the substance P and/or the neurokinin A receptor may be useful in the treatment of asthmatic disease (Frossard et al., *Life Sci.*, 49, 1941–1953 (1991); Advenier, et at., *Biochem. Biophys. Res. Comm.*, 184(3), 1418–1424 (1992)). These antagonists may also be useful in the treatment of emesis. See C. Bountra, K. Bounce, T. Dale, C. Gardner, C. Jordan, D. Twissell and P. Ward, *Eur. J. Pharmacol.*, 249, R3–R4 (1993) "Anti-emetic profile of a non-peptide neurokinin NK1 receptor antagonist", CP-99,994, in the ferret.

SUMMARY OF THE INVENTION

This invention is directed to compounds of Formula I.

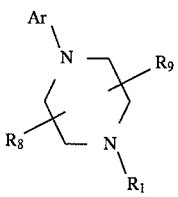

The invention is also concerned with pharmaceutical formulations with these novel compounds as active ingredients and the use of the novel compounds and their formulations in the treatment of certain disorders.

The compounds of this invention are tachykinin receptor antagonists and are useful in the treatment of inflammatory diseases, pain or migraine, asthma and emesis.

DETAILED DESCRIPTION OF THE INVENTION

In one embodiment, this invention is directed to compounds of Formula I

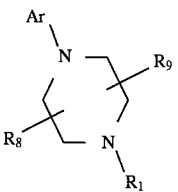

and pharmaceutically acceptable salts thereof, wherein the nitrogen attached to $R_1$ shown above is optionally quaternized with $C_{1-4}$alkyl or phenyl$C_{1-4}$alkyl or is optionally present as the N-oxide ($N^+O^-$), and wherein:

$R^1$ is selected from a group consisting of:

linear or branched $C_{1-8}$ alkyl, linear or branched $C_{2-8}$ alkenyl, wherein the $C_{1-8}$ alkyl or $C_{2-8}$ alkenyl is optionally mono, di, tri or tetra substituted, the substituents independently selected from:
(a) hydroxy,
(b) oxo,
(c) cyano,
(d) halogen which is defined to include Br, Cl, I, and F,
(e) trifluoromethyl,
(f) phenyl or mono, di or tri-substituted phenyl, the substituents independently selected from
  (1) phenyl,
  (2) hydroxy,
  (3) $C_{1-3}$alkyl,
  (4) cyano,
  (5) halogen,
  (6) trifluoromethyl,
  (7) —$NR_6COR_7$,
  (8) —$NR_6CO_2R_7$,
  (9) —$NR_6CONHR_7$,
  (10) —$NR_6S(O)_jR_7$, wherein j is 1 or 2,
  (11) —$CONR_6R_7$,
  (12) —$COR_6$,
  (13) —$CO_2R_6$,
  (14) —$OR_6$,
  (15) —$S(O)_kR_6$ wherein k is 0, 1 or 2,
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$,
(p) —$S(O)_kR_6$,
(q) heteroaryl, wherein heteroaryl is selected from the group consisting of:
  (1) benzimidazolyl,
  (2) benzofuranyl,
  (3) benzoxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (16) quinolyl,
  (17) tetrazolyl,
  (18) thiadiazolyl,
  (19) thiazolyl,
  (20) thienyl,
  (21) triazolyl,
wherein the heteroaryl is unsubstituted or mono di or tri-substituted, the substituents independently selected from:
  (a) phenyl,
  (b) hydroxy,
  (c) oxo,
  (d) cyano,
  (e) halogen,
  (f) trifluoromethyl;

Ar is selected from the group consisting of:
  (1) phenyl,
  (2) pyridyl,
  (3) pyrimidyl,
  (4) naphthyl,
  (5) furyl,
  (6) pyrryl,
  (7) thienyl,
  (8) isothiazolyl,
  (9) imidazolyl,
  (10) benzimidazolyl,
  (11) tetrazolyl,
  (12) pyrazinyl,
  (13) quinolyl,
  (14) isoquinolyl,
  (15) benzofuryl,
  (16) isobenzofuryl,
  (17) benzothienyl,
  (18) pyrazolyl,
  (19) indolyl,
  (20) isoindolyl,
  (21) purinyl,

(22) isoxazolyl,
(23) thiazolyl,
(24) oxazolyl,
(25) triazinyl, and
(26) benzthiazolyl,
(27) benzoxazolyl,
(28) imidazopyrazinyl,
(29) triazolopyrazinyl,
(30) naphthyridinyl,
(31) furopyridinyl,
(32) thiopyranopyrimidyl and the 5-oxide and 5-dioxide thereof,
(33) pyridazinyl,
(34) quinazolinyl,
(35) pteridinyl,
(36) triazolopyrimidyl,
(37) triazolopyrazinyl,
(38) thiapurinyl,
(39) oxapurinyl,
(40) deazapurinyl,
wherein Ar items (1) to (40) are optionally mono or di-substituted, said substituents being independently selected from:
  (a) $C_{1-3}$ alkyl, unsubstituted or substituted with
    (1) oxo,
    (2) hydroxy,
    (3) $OR_6$,
    (4) halogen,
    (5) trifluoromethyl,
    (6) phenyl or mono, di or tri-substituted phenyl, the substituents independently selected from hydroxy, cyano, halogen, and trifluoromethyl,
  (b) —$(CH_2)_n S(O)_k$—$(C_{1-6}$ alkyl), wherein n is 0, 1 or 2,
  (c) —$(CH_2)_n S(O)_j$—$NH_2$,
  (d) —$(CH_2)_n S(O)_j$—$NH(C_{1-6}$ alkyl),
  (e) —$(CH_2)_n S(O)_j$—$NHR_6$,
  (f) —$(CH_2)_n S(O)_j$—$NR_6$—$(C_{1-6}$ alkyl),
  (g) —$(CH_2)_n CONH_2$,
  (h) —$(CH_2)_n CONH$—$(C_{1-6}$ alkyl),
  (i) —$(CH_2)_n CONHR_6$,
  (j) —$(CH_2)_n CONR_6$—$(C_{1-6}$ alkyl),
  (k) —$(CH_2)_n CO_2H$,
  (l) —$(CH_2)_n CO_2$—$(C_{1-6}$ alkyl),
  (m) —$(CH_2)_n NR_6 R_7$,
  (n) —$(CH_2)_n NH$—$C(O)$—$C_{1-6}$alkyl,
  (o) —$(CH_2)_n NH$—$C(O)NH_2$,
  (p) —$(CH_2)_n NH$—$C(O)NHC_{1-6}$alkyl,
  (q) —$(CH_2)_n NH$—$C(O)N$-$(diC_{1-6}$ alkyl),
  (r) —$(CH_2)_n NH$—$S(O)_k$—$C_{1-6}$alkyl,
  (s) —$(CH_2)_n N(C_{1-3}$alkyl)—$C(O)$—$N(diC_{1-6}$ alkyl),
  (t) —$(CH_2)_n$-heteroaryl or —$C(O)$-heteroaryl or —$(CH_2)_n$—O-heteroaryl, wherein the heteroaryl is selected from the group consisting of:
    (1) benzimidazolyl,
    (2) benzofuranyl,
    (3) benzoxazolyl,
    (4) furanyl,
    (5) imidazolyl,
    (6) indolyl,
    (7) isooxazolyl,
    (8) isothiazolyl,
    (9) oxadiazolyl,
    (10) oxazolyl,
    (11) pyrazinyl,
    (12) pyrazolyl,
    (13) pyridyl or oxopyridyl,
    (14) pyrimidyl,
    (15) pyrrolyl,
    (16) quinolyl,
    (17) tetrazolyl,
    (18) thiadiazolyl,
    (19) thiazolyl,
    (20) thienyl,
    (21) triazolyl, wherein the heteroaryl group of items (1) to (21) is unsubstituted, mono, di or tri substituted, the substituents selected from:
      (a) hydrogen,
      (b) $C_{1-6}$ alkyl, branched or unbranched, unsubstituted or mono or di-substituted, the substituents being selected from hydrogen and hydroxy,
      (c) hydroxy,
      (d) oxo,
      (e) $OR_6$,
      (f) halogen,
      (g) trifluoromethyl,
      (h) nitro,
      (i) cyano,
      (j) —$NHR_6$,
      (k) —$NR_6 R_7$,
      (l) —$NHCOR_6$,
      (m) —$NR_6 COR_7$,
      (n) —$NHCO_2 R_6$,
      (o) —$NR_6 CO_2 R_7$,
      (p) —$NHS(O)_j R_6$,
      (q) —$NR_6 S(O)_j R_7$,
      (r) —$CONR_6 R_7$,
      (s) —$COR_6$,
      (t) —$CO_2 R_6$,
      (u) —$S(O)_j R_6$;
$R_6$ is
  (1) hydrogen,
  (2) $C_{1-6}$ alkyl, or mono or di-substituted $C_{1-6}$ alkyl, the substituents independently selected from:
    (a) phenyl,
    (b) hydroxy,
    (c) oxo,
    (d) cyano,
    (e) halogen,
    (f) trifluoromethyl,
  (3) phenyl or mono di or tri-substituted phenyl, the substituents independently selected from:
    (a) hydroxy,
    (b) $C_{1-3}$alkyl,
    (c) cyano,
    (d) halogen,
    (e) trifluoromethyl,
$R_7$ is
  (1) hydrogen,
  (2) $C_{1-6}$ alkyl, or mono or di-substituted $C_{1-6}$ alkyl, the substituents independently selected from:
    (a) phenyl unsubstituted or substituted with
      (1) hydroxy,
      (2) $C_{1-3}$alkyl,
      (3) cyano,
      (4) halogen,
      (5) trifluoromethyl,
      (6) $C_{1-3}$alkyloxy,
    (b) hydroxy,
    (c) oxo, (d) cyano,
(e) halogen,
(f) trifluoromethyl, (3) phenyl or mono di or tri-substituted phenyl, the substituents independently selected from:
(a) hydroxy,
(b) $C_{1-3}$alkyl,
(c) cyano,
(d) halogen,
(e) trifluoromethyl, (4) naphthyl or mono di or tri-substituted naphthyl, the substituents independently selected from:
(a) hydroxy,
(b) $C_{1-3}$alkyl,
(c) cyano,
(d) halogen,
(e) trifluoromethyl, (5) $C_{1-3}$alkyloxy, or $R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
(1) hydroxy,
(2) oxo,
(3) cyano,
(4) halogen,
(5) trifluoromethyl, $R_8$ and $R_9$ are each independently hydrogen or substituted $C_{1-4}$alkyl wherein the substitutent is selected from the group consisting of
(1) hydroxy,
(2) hydrogen,
(3) cyano,
(4) halogen,
(5) trifluoromethyl,
(6) $C_{1-3}$alkyloxy, provided that when Ar is phenyl, pyridyl or pyrimidyl then Ar is mono di or tri-substituted, and further provided that when Ar is mono substituted phenyl then the substituent is other than halo, hydroxy, —$OC_{1-4}$alkyl, $CF_3$ or $C_{1-4}$alkyl, and further provided that when Ar is di- or tri-substituted, at least one of the substituents is other than halo, hydroxy, —$OC_{1-4}$alkyl, $CF_3$ or $C_{1-4}$alkyl.

One genus within this embodiment is the compounds of Formula I wherein:

$R_1$ is selected from a group consisting of:

$C_3$, $C_4$, $C_5$, $C_6$, $C_7$, $C_8$ linear or branched alkyl, unsubstituted or mono, di or tri-substituted, the substituents independently selected from:
(a) hydroxy,
(b) Cl or F,
(c) phenyl or mono, di or tri-substituted phenyl, the substituents independently selected from:
(1) phenyl,
(2) hydroxy,
(3) $C_{1-3}$alkyl,
(4) cyano,
(5) halogen,
(6) trifluoromethyl,
(d) —$NR_6COR_7$, wherein $R_6$ is hydrogen or $C_{1-3}$ alkyl and $R_7$ is phenyl optionally substituted with Cl, F, $CF_3$ or $C_{1-3}$alkyl,
(e) —$NHS(O)_jR_6$,
(f) —$COR_6$,
(h) —$OR_6$, Ar is selected from the group consisting of:
(1) phenyl,
(2) pyrazinyl,
(3) pyrazolyl,
(4) pyridyl,
(5) pyrimidyl, and
(6) thienyl,
wherein Ar is unsubstituted or mono or di-substituted, the substituents independently selected from
(a) $C_{1-3}$ alkyl, unsubstituted or substituted with
(1) oxo,
(2) hydroxy,
(3) $OR_6$,
(4) halogen,
(5) trifluoromethyl,
(b) $CONR_6$—($C_{1-2}$ alkyl),
(c) $CO_2H$,
(d) $CO_2$—($C_{1-2}$ alkyl),
(e) $CH_2NR_6$—($C_{1-2}$ alkyl),
(f) $CH_2NH$—$C(O)$—$C_{1-3}$alkyl,
(h) $CH_2NH$—$C(O)NH_2$,
(i) $CH_2NH$—$C(O)NHC_{1-3}$alkyl,
(j) $CH_2NH$—$C(O)N$-$diC_{1-3}$ alkyl),
(k) $CH_2NH$—$S(O)_j$—$C_{1-3}$alkyl,
(l) $CH_2$-heteroaryl group, with the heteroaryls selected from the group consisting of:
(1) imidazolyl,
(2) oxazolyl,
(3) pyridyl,
(4) tetrazolyl,
(5) triazolyl, the heteroaryl group is unsubstituted, mono, di or tri-substituted, the substituents selected from:
(a) hydrogen,
(b) $C_{1-6}$ alkyl, branched or unbranched, unsubstituted or mono or di-substituted, the substituents being selected from hydrogen and hydroxy; and $R_9$ is hydrogen.

One class of compounds within this genus is the compounds of Formula I wherein:

Ar is mono substituted or di-substituted phenyl wherein the substituents are selected from the group consisting of:
(a) $C_{1-3}$ alkyl, unsubstituted or substituted with
(1) oxo,
(2) hydroxy,
(3) $OR_6$,
(b) —$CH_2NR_6$—($C_{1-2}$ alkyl),
(c) —$CH_2NH$—$C(O)$—$C_{1-3}$alkyl,
(d) —$CH_2NH$—$C(O)NH_2$,
(i) —$CH_2NH$—$C(O)NHC_{1-3}$alkyl,
(j) —$CH_2NH$—$C(O)N$-$diC_{1-3}$ alkyl),
(k) —$CH_2NH$—$S(O)_j$—$C_{1-3}$alkyl,
(l) —$CH_2$-heteroaryl group, with the heteroaryls selected from the group consisting of:
(1) imidazolyl,
(2) oxazolyl,
(3) pyridyl,
(4) tetrazolyl,
(5) triazolyl, the heteroaryl group is unsubstituted, mono, di or tri substituted, the substituents selected from:
(a) hydrogen, (b) $C_{1-6}$ alkyl, branched or unbranched, unsubstituted or mono or disubstituted, the substituents being selected from hydrogen and hydroxy.

Illustrating the invention are the compounds wherein Ar is selected from

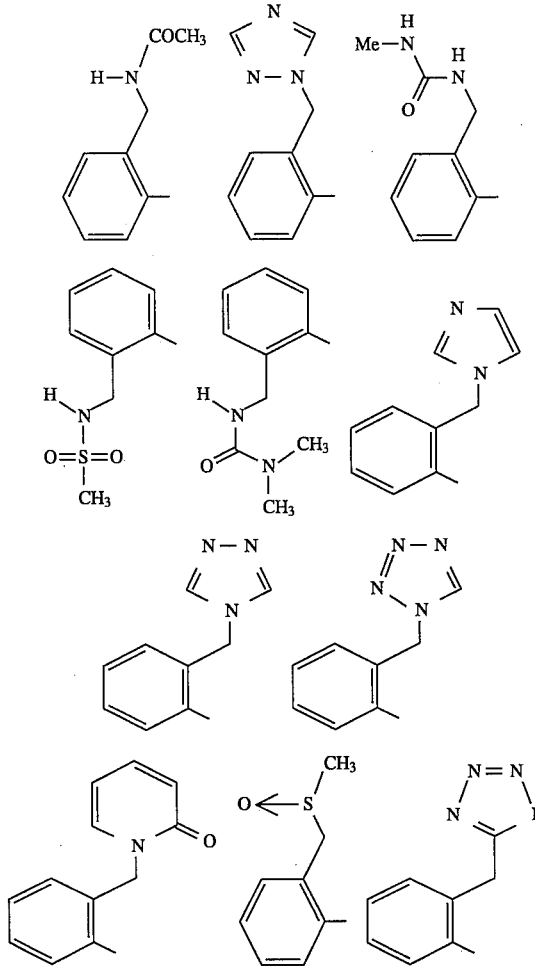

A second genus of this invention encompasses the compounds of Formula I wherein Ar is selected from the group consisting of:

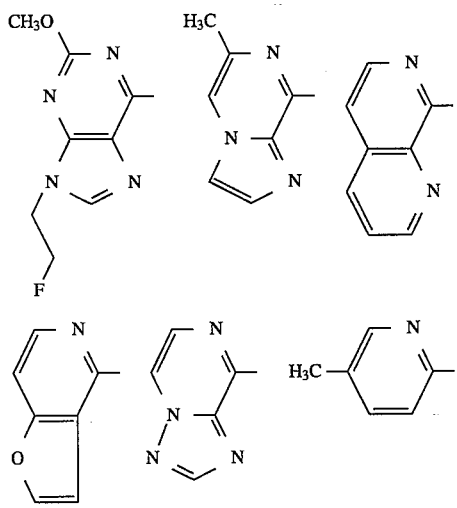

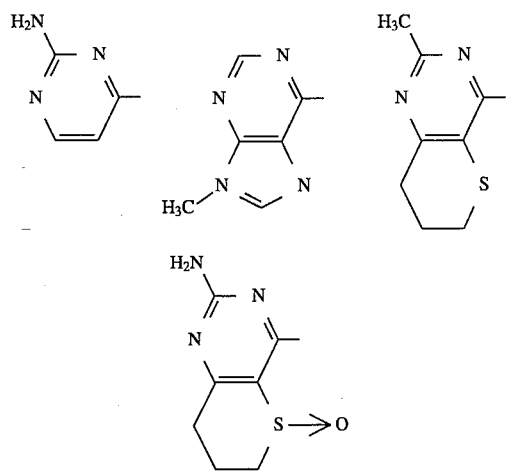

Illustrating the invention are the following compounds as well as those listed in Table 1:

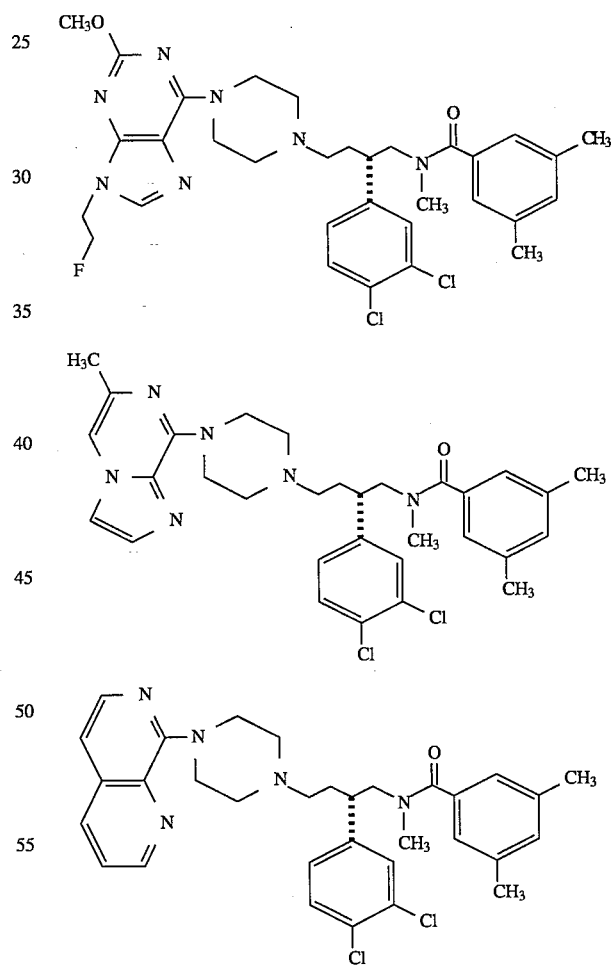

11
-continued
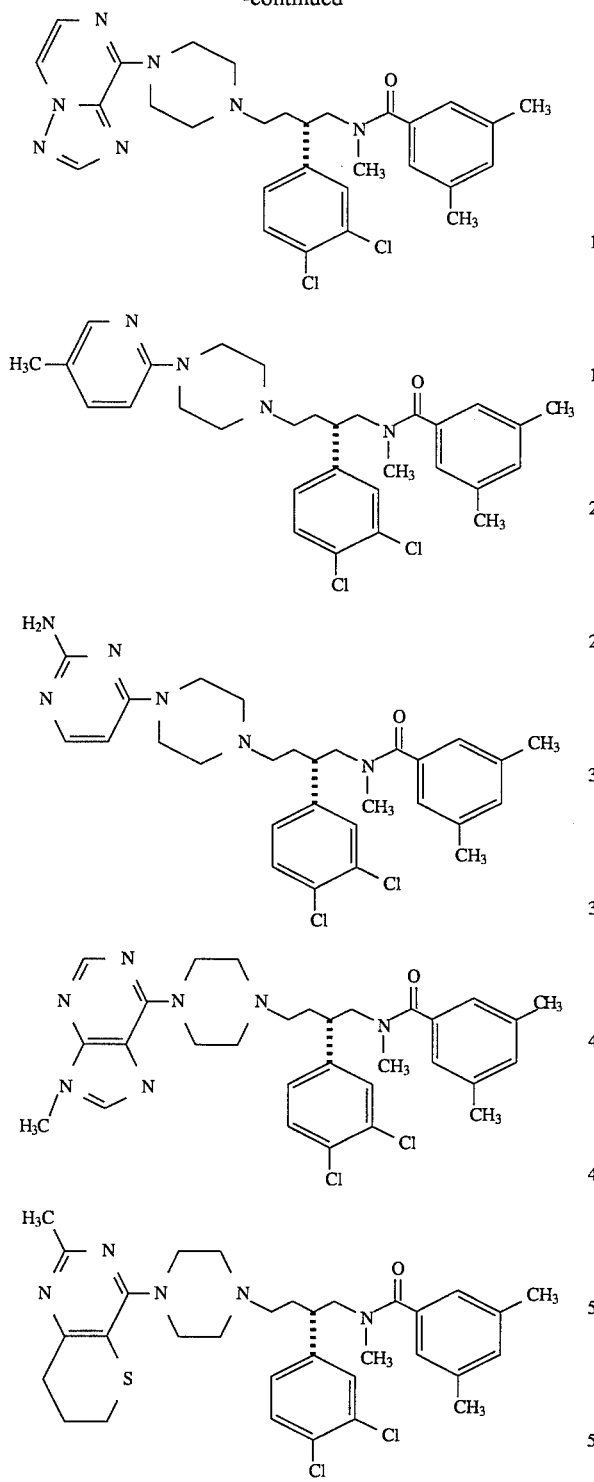
12
-continued
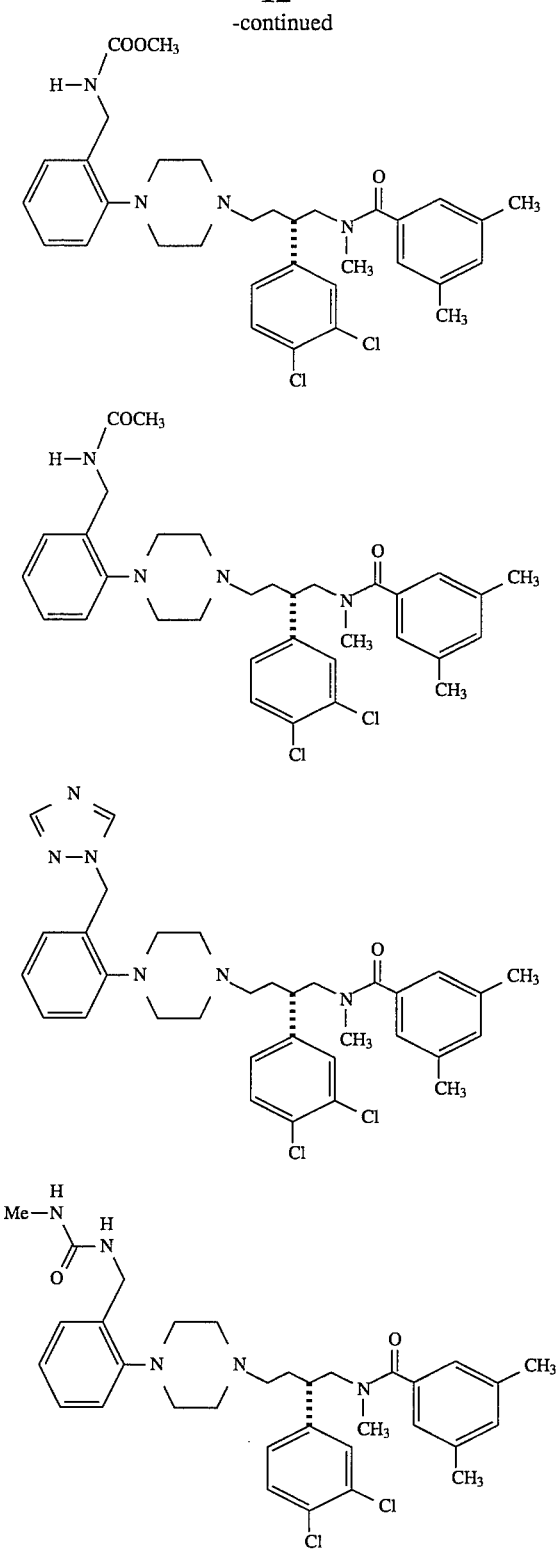

13
-continued
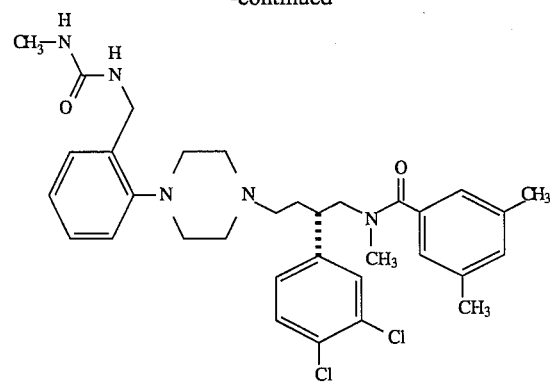
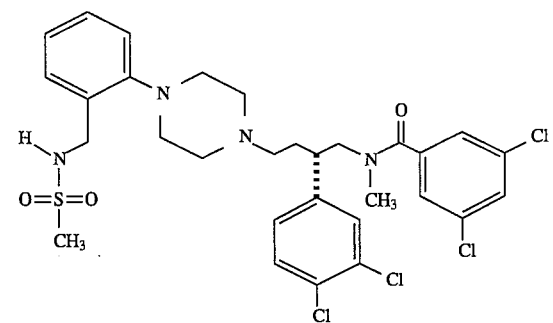
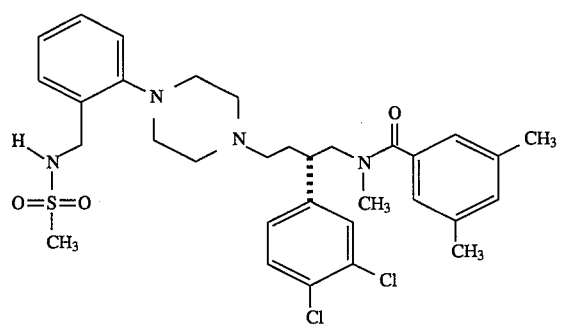
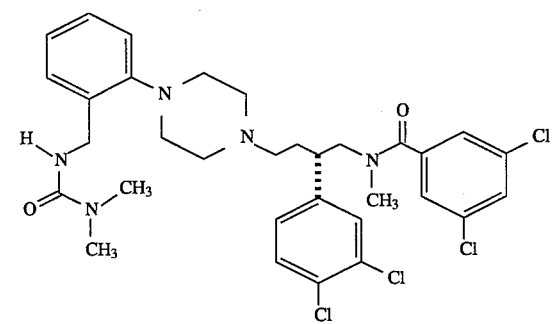
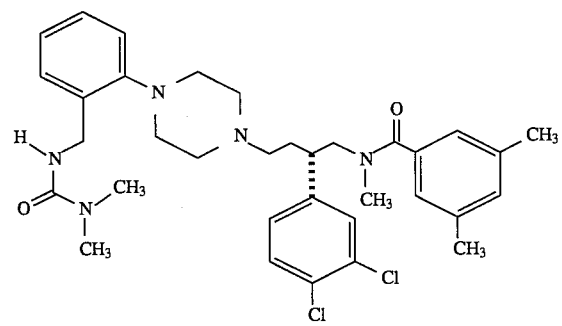
14
-continued
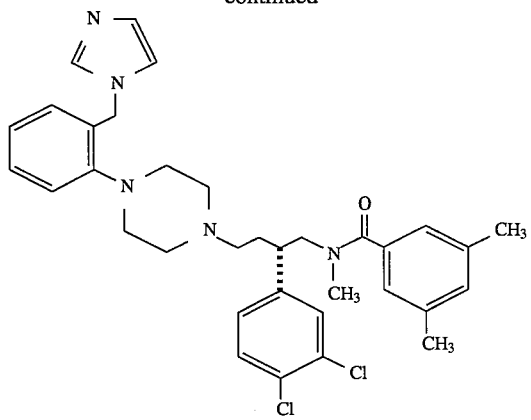
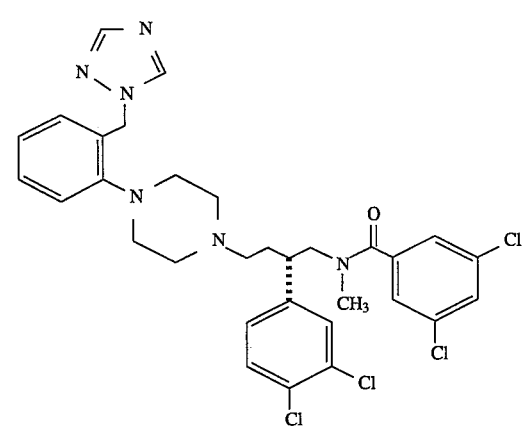
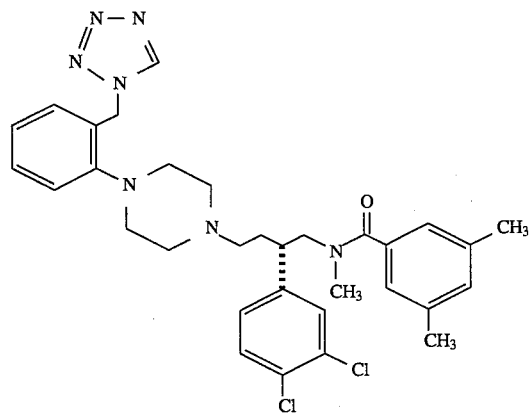
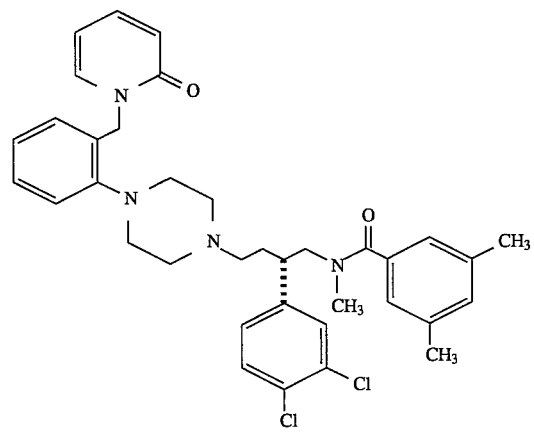

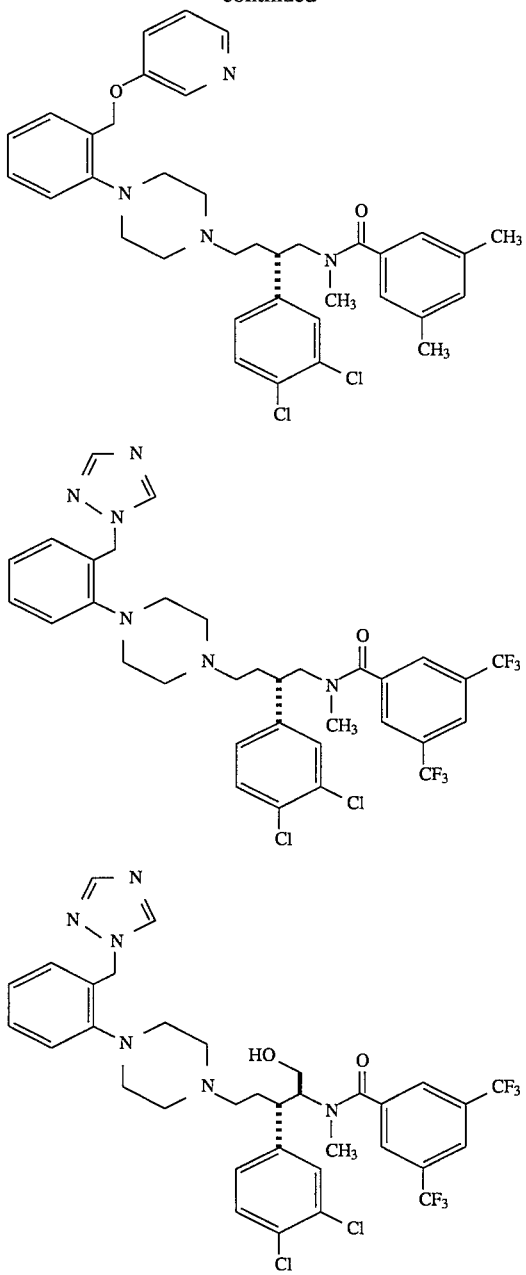

As appreciated by those of skill in the art, halo as used herein are intended to include chloro, fluoro, bromo and iodo. Similarly, C1–6, as in $C_{1-6}$alkyl is defined to identify the group as having 1, 2, 3, 4, 5, or 6 carbons, such that $C_{1-6}$alkyl specifically includes methyl, ethyl, propyl, butyl, pentyl or hexyl Exemplifying the invention are the compounds of the Examples 1–32.

In an alternative embodiment the compounds of formula I are co-administered with a β2-agonist such as: Bambuterol, U.S. Pat. No. 4,419,364 issued to Draco on Dec. 6, 1983; Bitolterol mesylate, U.S. Pat. No. 4,138,581 issued to Sterling Feb. 6, 1979; Carbuterol, U.S. Pat. No. 3,763,232 issued to Smith Kline Oct. 2, 1973; Clenbuterol, U.S. Pat. No. 3,536,712 issued to Boehringer Ingelheim Oct. 27, 1970; Dopexamine, U.S. Pat. No. 4,645,768 issued to Fisons Feb. 24, 1987; Formoterol, U.S. Pat. No. 3,994,974 issued to Yamanouchi Nov. 30, 1976; Mabuterol, U.S. Pat. No. 4,119, 710 issued to Boehringer Ingelheim Oct. 10, 1978; Pirbuterol hydrochloride U.S. Pat. No. 3,700,681 issued to Pfizer Oct. 24, 1972; Procaterol hydrochloride U.S. Pat. No. 4,026,897 issued to Otsuka May 31, 1977; Ritodrine hydrochloride U.S. Pat. No. 3,410,944 issued to North American Philips Nov. 12, 1968; Brosaterol, U.S. Pat. No. 4,276,299 issued to Zambon Jun. 30, 1981 and U.S. Pat. No. 4,520,200 issued to Zambon May 28, 1985; Cimaterol, U.S. Pat. No. 4,407,819 issued to American Cyanamid Oct. 4, 1983; Docarpamine, U.S. Pat. No. 4,228,183 issued to Tanabe Oct. 14, 1980; Salmeterol, U.S. Pat. No. 4,992,474 issued to Glaxo Feb. 21, 1991 and U.S. Pat. No. 5,091,422 issued to Glaxo Feb. 25, 1992.

The compounds of Formula I are particularly useful in the treatment of diseases or conditions that are advantageously treated by contomitant antagonism of both NK1 and NK2 receptors or NK1, NK2 and NK3 receptors. These diseases include neuropathy, such as diabetic or peripheral neuropathy and chemotherapy-induced neuropathy; asthma; osteoarthritis; rheumatoid arthritis; and migraine.

In a second alternative embodiment the compounds of Formula I may be co-administered with another NK1 or NK2 antagonist such as those described in:

Appln No. DO-139125, filed 08 Jun. 1978, Pub. 12 Dec. 1979;
Appln No. EP-82568, filed 22 Dec. 1981, Pub. 29 Jun. 1983;
Appln No. EP-490379, filed 13 Dec. 1990, Pub. 17 Jun. 1992;
Appln No. EP-353732, filed 05 Aug. 1988, Pub. 07 Feb. 1990;
Appln No. EP-161007, filed 13 Jan. 1984, Pub. 13 Nov. 1985;
Appln No. EP-385-43, filed 28 Feb. 1989, Pub. 05 Sep. 1990;
Appln No. WO8301251, filed 09 Oct. 1981, Pub. 14 Apr. 1983;
Appln No. BE-894602, filed 09 Oct. 1981, Pub. 31 Jan. 1983;
Appln No. DE3205991, filed 19 Feb. 1982, Pub. 01 Sep. 1983;
Appln No. EP-327009, filed 02 Feb. 1988, Pub. 09 Aug. 1989;
Appln No. EP-336230, filed 05 Apr. 1988, Pub. 11 Oct. 1989;
Appln No. 394989, filed 28 Apr. 1989, Pub. 31 Oct. 1990;
Appln No. AU9068010, filed 22 Dec. 1989, Pub. 27 Jun. 1991;
Appln No. EP-482539, filed 24 Oct. 1990, Pub. 29 Apr. 1992;
Appln No. EP-443132, filed 10 Dec. 1990, Pub. 28 Aug. 1991;
Appln No. EP-498069, filed 21 Dec. 1990, Pub. 12 Aug. 1992;
Appln No. WO9222569, filed 19 Jun. 1991, Pub. 23 Dec. 1992;
Appln No. JO4297492, filed 24 Oct. 1991, Pub. 21 Oct. 1992;
U.S. Pat. No. 4,997,853, filed 02 Dec. 1988, Pub. 05 Mar. 1991;
Appln No. EP-272929, filed 24 Dec. 1986, Pub. 29 Jun. 1988;
Appln No. EP-360390, filed 25 Jul. 1988, Pub. 28 Mar. 1990;
U.S. Pat. No. 3,862,114, filed 22 Nov. 1971, Pub. 21 Jan. 1975;
Appln No. EP-219258, filed 30 Sep. 1985, Pub. 22 Apr. 1987, U.S. Pat. No. 4,742,156, filed 30 Sep. 1985, Pub. 03 May 1988;
Appln No. EP-401177, filed 29 May 1989, Pub. 05 Dec. 1990;
Appln No. WO9202546, filed 03 Aug. 1990, Pub. 20 Feb. 1992;
Appln No. EP-176436, filed 26 Sep. 1984, Pub. 02 Apr. 1986;
U.S. Pat. Ser. No. 4,680,283, filed 26 Sep. 1984, Pub. 14 Jul. 1987;
Appln No. WO9220661, filed 22 May 1991, Pub. 26 Nov. 1992;
Appln No. EP-520555, filed 24 Jun. 1991, Pub. 30 Dec. 1992;
Appln No. EP-347802, filed 20 Jun. 1988, Pub. 27 Dec. 1989;
Appln No. EP-412542, filed 10 Aug. 1989, Pub. 13 Feb. 1991;
Appln No. WO9005729, filed 23 Nov. 1988, Pub. 31 May 1990;
Appln No. WO9005525, filed 23 Nov. 1988, Pub. 31 May 1990;
Appln No. EP-436334, filed 04 Jan. 1990, Pub. 10 Jul. 1991;
Appln No. WO9118878, filed 31 May 1990, Pub. 12 Dec. 1991;
Appln No. WO9118899, filed 01 Jun. 1990, Pub. 12 Dec. 1991;
Appln No. WO9201688, filed 23 Jul. 1990, Pub. 06 Feb. 1992;
Appln No. WO9206079, filed 28 Sep. 1990, Pub. 16 Apr. 1992;
Appln No. WO9212152, filed 03 Jan. 1991, Pub. 23 Jul. 1992;
Appln No. WO9212151, filed 10 Jan. 1991, Pub. 23 Jul. 1992;
WO9215585, filed 01 Mar. 1991, Pub. 29 Apr. 1992;
Appln No. WO022-676, filed 22 May 1991, Pub. 26 Nov. 1992;
Appln No. WO9221677, filed 31 May 1991, Pub. 10 Dec. 1992;
Appln No. WO9300331, filed 20 Jun. 91, Pub. 07 Jun. 1993;
Appln No. WO9300330, filed 21 Jun. 91, Pub. 07 Jan. 1993;
Appln No. WO9109844, filed 11 Jul. 1991, Pub. 11 Jul. 1991;
Appln No. EP-429366, filed 23 Nov. 1989, Pub. 29 May 1991;
Appln No. EP-430771, filed 23 Nov. 1989, Pub. 05 Jun. 1991;
Appln No. EP-514274, filed 17 May 1991, Pub. 19 Nov. 1992;
Appln No. EP-514276, filed 17 May 1991, Pub. 19 Nov. 1992;
Appln No. EP-514275, filed 17 May 1991, Pub. 19 Nov. 1992;
Appln No. EP-514273, filed 17 May 1991, Pub. 19 Nov. 1992;
Appln No. EP-428434, filed 06 Nov. 1989, Pub. 22 May 1991;
Appln No. EP-474561, filed 09 May 1990, Pub. 11 Mar. 1992;
Appln No. EP-512901, filed 03 May 1991, Pub. 11 Nov. 1992;
Appln No. EP-512902, filed 03 May 1991, Pub. 11 Nov. 1992;
Appln No. EP-515240, filed 03 May 1991, Pub. 25 Nov. 1992;
U.S. Pat. No. 4,472,305, filed 17 May 1983, Pub. 18 Sep. 1984;
U.S. Pat. No. 4,839,465, filed 20 Jan. 1987, Pub. 13 Jun. 1989;
Appln No. EP-101929, filed 28 Jul. 1982, Pub. 07 Mar. 1984;
Appln No. WO9102745, filed 16 Aug. 1989, Pub. 07 Mar. 1991;
U.S. Pat. No. 3,912,711, filed 03 Jul. 1972, Pub. 14 Oct. 1975;
U.S. Pat. No. 4,059,693, filed 11 Jun. 1976, Pub. 22 Nov. 1977;
U.S. Pat. No. 4,481,139, filed 13 Apr. 1983, Pub. 06 Nov. 1984;
U.S. Pat. No. 7,358,073, filed 24 Oct. 1988, Pub. 19 Dec. 1989;
U.S. Pat. No. 7,261,627, filed 24 Oct. 1988, Pub. 07 Mar. 1989, which are hereby incorporated by reference.

In a third alternative embodiment the compounds of Formula I can be co-administered with a leucotriene antagonist, such a leucotriene $D_4$ antagonist, exemplified by those disclosed in EP O 480,717, published Apr. 15, 1992; U.S. Pat. No. 5,270,324, issued Dec. 14, 1993; EP O 604,114, published Jun. 1994; and U.S. Pat. No. 4,859,692, issued Aug. 22, 1989. This combination is particularly useful in the treatment of respiratory diseases such as asthma, chronic bronchitis and cough.

In a fourth embodiment the compounds of Formula I may be used in combination with a aerosolized corticosteroid such as Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

The compounds of Formula I are useful in the prevention and treatment of a wide variety of clinical conditions (as detailed in this specification) which are characterized by overstimulation of the tachykinin receptors, in particular NK1, NK2 and NK3.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease, irritable bowel syndrome, incontinence, nausea, and emesis, including acute, delayed, post-operative, late-phase, and anticipatory emesis, such as emesis induced by for example chemotherapy, radiation, surgery, migraine, toxins, such as metabolic or microbial toxins, viral or bacterial infections, pregnancy, vestibular disorder, motion, mechanical stimulation, psychological stress or disturbance, high altitude, weightlessness, intoxication, resulting for example from consumption of alcohol, and variations in intercranial pressure, in particular, for example, drug or radiation induced emesis or post-operative nausea and vomiting; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK1, NK2 and NK3.

The compounds of the present invention are particularly useful in the treatment of pain or nociception and/or inflammation and disorders associated therewith such as, for example: neuropathy, such as diabetic or peripheral neuropathy and chemotherapy-induced neuropathy; asthma; osteoarthritis; rheumatoid arthritis; and migraine.

For the treatment of any of these diseases compounds of Formula I may be administered orally, topically, parenterally, ICV, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oil, or a mineral oil, for example, liquid paraffin or mixtures of these. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.001 to 25 mg/kg per day, about 0.005 to 10 mg/kg per day, or about 0.005 to 5 mg/kg per day. Within this range the dosage may be 0.005 to 0.05, 0.05 to 0.5 or 0.5 to 5.0 mg/kg per day. The compounds may be administered on a regimen of 1 to 4 times per day, preferably once or twice per day.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 μg of the plasmid DNA into 10 million COS cells was achieved by electroporation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM HEPES pH$_{7.4}$) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% CO$_2$ at 37° C. for three days before the binding assay. Similar methods were used to express the NK2 receptor.

B. Stable Expression in CHO

To establish a stable cell line expressing the cloned human NK1R, the cDNA was subcloned into the vector pRcCMV (INVITROGEN). Transfection of 20 μg of the plasmid DNA into CHO cells was achieved by electroporation in 800 μl of transfection buffer supplemented with 0.625 mg/ml Herring sperm DNA at 300 V and 950 uF using the IBI GENEZAPPER (IBI). The transfected cells were incubated in CHO media (10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)) in 5% CO$_2$ at 37° C. until colonies were visible. Each colony was separated and propagated. The cell clone with the highest number of human NK1R was selected for subsequent applications such as drug screening.

Similar methods were used to express the human NK2 receptor.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH$_{7.5}$, 5 mM MnCl$_2$, 150 mM NaCl, 0.04 mg/ml bacitracin, 0.004 mg/ml leupeptin, 0.02 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 500 ul of cells were added to a tube containing 20 μl of 1.5 to 0.25 nM of $^{125}$I-SP and 5 μl of unlabeled substance p or any other test compound in DMSO. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM MnCl$_2$, 150 mM NaCl) three times and its radioactivity was determined by gamma counter. A similar assay was used for NK2 except $^{125}$I-NKA was used as the ligand.

The activation of phospholipase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with CHCl$_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate—0.1N formic acid and quantitated by beta counter. similar methods were used to assess antagonism at the NK2 receptor, except NKA was used as the stimulating agonist.

The compounds of Formula I as Exemplified in the EXAMPLES below have been found to displace radioactive ligand for the NK-1 receptor at a concentration range of 0.01 nM to 1.0 μM, for the NK-2 receptor, 0.01 nM to 5 μM, and for the NK-3 receptor, 1.0 nM to 10 μM. For comparison the activity of FK-224 is disclosed in Ichinoe, M. et al., *Lancet*, vol. 340, pp 1248–1251 (1992).

TABLE 1

Piperazine Compounds as NK₁-NK₂ and NK₃ Antagonists

| $R_a$ | $R_b$ | $R_c$ | $NK_1$ | $NK_2$ | $NK_3$ |
|---|---|---|---|---|---|
| (H₃CO-substituted imidazo-pyrazine with F-ethyl) | 3,4-diCl₂ | CH₃ | 0.45 nM | 9 nM | 25 nM |
| (CH₃O-substituted imidazo-pyrazine with CH₃O-methyl) | 3,4-diCl | CH₃ | 1 nM | 20 nM | 200 nM |
| (imidazo-pyrazine with H₃C-N) | 3,4-diCl | CH₃ | 0.2 nM | 10 nM | 60 nM |
|  | 4-Cl | CH₃ | 2.5 nM | 25 nM | 60 nM |
| (H₃C-substituted imidazo-pyrazine) | 3,4-diCl | CH₃ | 0.6 nM | 15 nM | 300 nM |
| (naphthyridine) | 3,4-diCl | CH₃ | 0.45 nM | 20 nM | 150 nM |
| (triazolopyrazine) | 3,4-diCl | CH₃ | 0.9 nM | 5 nM | 60 nM |
|  | 3,4-diCl | CF₃ | 0.9 nM | 12 nM | 640 nM |
|  | 4-Cl | CF₃ | 2.4 nM | 14 nM | 173 nM |

TABLE 1-continued
Piperazine Compounds as NK$_1$–NK$_2$ and NK$_3$ Antagonists
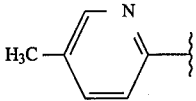
| R$_a$ | R$_b$ | Rc | NK$_1$ | NK$_2$ | NK$_3$ |
|---|---|---|---|---|---|
| 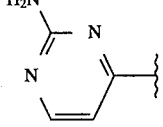 | 3,4-diCl | CH$_3$ | 1.5 nM | 40 nM | 250 nM |
| 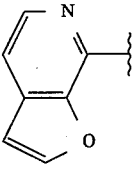 | 3,4-diCl | CH$_3$ | 0.8 nM | 35 nM | 450 nM |
| 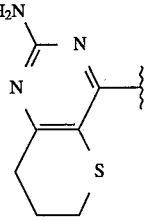 | 3,4-diCl | CH$_3$ | 0.65 nM | 35 nM | 140 nM |
| 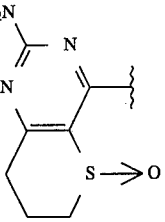 | 3,4-diCl | CH$_3$ | 0.9 nM | 25 nM | 50 nM |
| 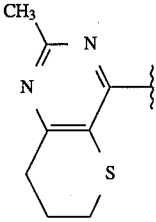 | 3,4-diCl | CH$_3$ | 2 nM | 10 nM | 130 nM |
|  | 3,4-diCl | CH$_3$ | 0.3 nM | 15 nM | 55 nM |

TABLE 1-continued

Piperazine Compounds as NK$_1$–NK$_2$ and NK$_3$ Antagonists

| R$_a$ | R$_b$ | Rc | NK$_1$ | NK$_2$ | NK$_3$ |
|---|---|---|---|---|---|
| (CH$_3$-pyridyl-S→O group) | 3,4-diCl | CH$_3$ | 1.5 nM | 30 nM | 300 nM |

Several methods for preparing the compounds of this invention are illustrated in the following Schemes and Examples. Starting materials are made from known procedures or as illustrated. Substituted purines may be prepared as disclosed in U.S. Pat. No. 5,057,517; imidazo(1.2-a)pyrazinyl, as disclosed in U.S. Pat. No. 4,242,344; (1,2,4)triazolo(1.5-a)pyrazinyl as disclosed in *J. Org. Chem*, 1974, 39, 2143 and *J.C.S. Perkin I*, 1980, 506; 1,7-naphthyridinyl as disclosed in *J. Org. Chem.* 1963, 28, 1753; furo(3.2-c)pyridinyl as disclosed in *J. Heterocyclic Chem.*, 1982, 19, 1207; and substituted 6-H-7,8-dihydrosthiopyrano(3.2-d)pyrimidyl as disclosed in *Arch. Int. Pharmacodyn.* 1986, 280, pp302–313. As appreciated by those of skill in the art, compounds bearing the substituents R$_8$ and R$_9$ may be prepared essentially as described in the Schemes.

The compounds of the present invention are prepared by alkylating piperazine 1 (R$_1$=H) under appropriate conditions (Scheme 1). In one method illustrated by Example 1, Step E, piperazine 1 (R$_1$=H) is combined with the appropriate aldehyde and the intermediate imine is reduced to the amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Examples 1 Step A by Hale, J. J.; Finke, P. E.; MacCoss, M. *Bioorganic and Medicinal Chemistry Letters* 1993 3, 319–322.

In an alternative embodiment of the present invention, piperazine 1 (R$_1$=H) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J., *Advanced Organic Chemistry*, 3rd ed., John Wiley & Sons, New York, pp. 382–384 (1985), or alkyl sulfonate ester using methods described in March J., *Advanced Organic Chemistry*, 3rd ed., John Wiley & Sons, New York, p. 444 (1985).

In an alternative embodiment of the present invention, 1 (R$_1$=H) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I. The product amide can in and of itself be a neurokinin antagonist or can be reduced with a strong reducing agent, such as diborane or lithium aluminum hydride, to give the tertiary amine.

SCHEME I

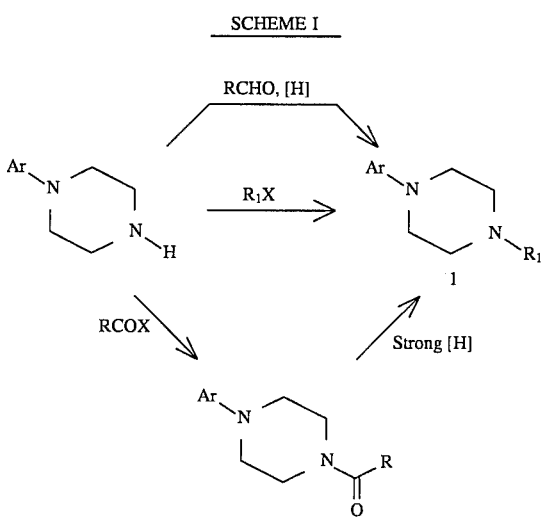

Optionally, Compound 1 formed in the alkylation step may be further modified in subsequent reactions. In one illustration of such an approach, the piperazine fragment may contain a nitro group, which is reduced to the amine after the coupling step. The resulting amine is further modified by acylation to provide the desired compounds. The piperazine fragment may also contain a protecting group such as a benzyl ester or a t-butyl ester. After reductive amination the protecting group is removed and the resulting acid is further reacted to provide additional analogs. Alternatively, the aldehyde portion may also contain a protecting group such as a t-butoxycarbonyl for an amino function. After reductive amination, the t-butoxycarbonyl group is removed by treatment with a strong acid such as trifluoroacetic acid, formic acid or hydrochloric acid and the resulting amine may be acylated to provide other analogs.

The piperazine starting materials used in the coupling reaction are prepared using methods described in the literature; more specifically as described in Meurer, U.S. Pat. Nos. 5,057,517; 4,242,344; *J. Org. Chem,* 1974, 39, 2143 and *J.C.S. Perkin I,* 1980, 506; *J. Org. Chem.* 1963, 28, 1753; *J. Heterocyclic Chem.,* 1982, 19, 1207; *Arch. Int. Pharmacodyn.* 1986, 280, pp302–313; Meurer, L. C. et al., *J. Med. Chem.,* 1992, 35, 3845–3857.None of these published compounds are claimed to be neurokinin antagonists. Alternatively, the piperazine substrates can be prepared as illustrated in Schemes 2–4.

Substituted 4-arylpiperazines can be prepared from appropriate fluorobenzene derivative as shown in Scheme 2. Thus, reaction of 2-fluorobenzonitrile with 1-t-butoxycarbonylpiperazine in the presence of a base such as $K_2CO_3$ gives 1-t-butoxycarbonyl-4-(2-cyanophenyl)-piperazine. Reduction of the cyano group by hydrogenation in the presence of Raney nickel or by other known methods gives a benzyl amine which can be acylated (Example 1, Step D). The t-butoxycarbonyl protecting group is removed by treatment with trifluoroacetic acid or anhydrous HCl to give a piperazine which can be used in the reductive amination step (Example 1, Step E). Similar reactions using 2-chloronitrobenzene in the place of 2-fluorobenzonitrile can provide compounds containing a substituted aniline. Analogs containing a benzoic acid or its derivatives can be prepared by substituting 2-fluorobenzoic acid in this sequence.

SCHEME 2

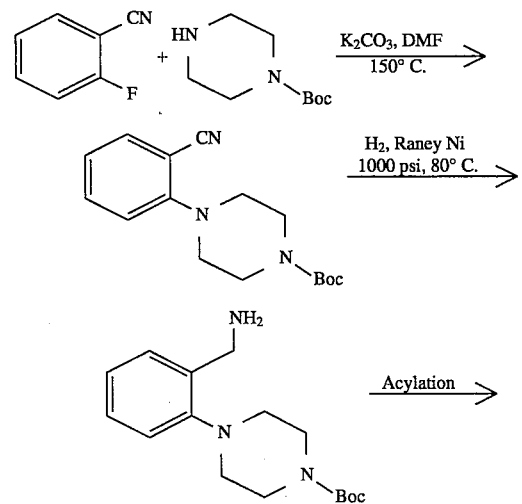

SCHEME 2 -continued

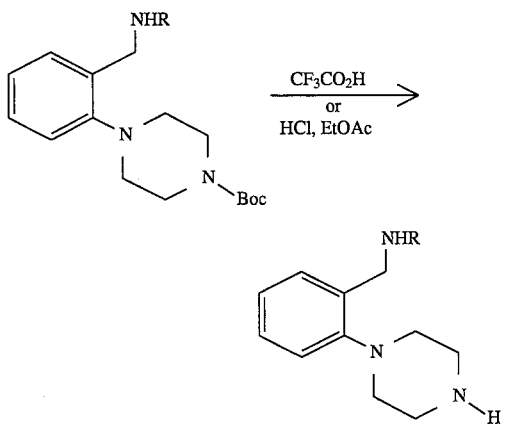

Arylpiperazine derivatives containing heterocyclic substituents can be synthesized as shown in Scheme 3. Reaction between 2-fluorobenzaldehyde and 1-t-butoxycarbonylpiperazine as described above gives 1-t-butoxycarbonyl-4-(2-formylphenyl)-piperazine (Example 9, Step A). Reduction of the aldehyde and treatment of the resulting alcohol with methanesulfonyl chloride gives a mesylate, while treatment of the alcohol with triphenylphosphine and carbon tetrabromide gives the bromide. Displacement of the mesylate by a heterocycle such as imidazole (Example 9, Step C) in the presence of a base and removal of the t-butoxycarbonyl protecting group furnishes piperazine which is used in the coupling reactions described in Scheme I.

SCHEME 3

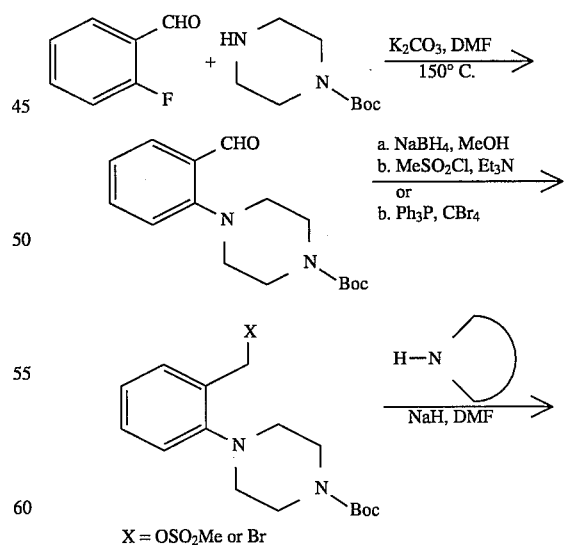

X = OSO₂Me or Br

-continued
SCHEME 3

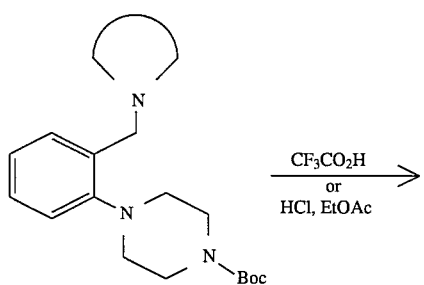

Preparation of piperazines containing a heteroaryl substituent is outlined in Scheme 4. Reaction of 1-t-butoxycarbonylpiperazine with a chloro substituted heteroaromatic compound such as 8-chloro-1,7-naphthyridine (Example 22, Step A) or 8-chloro-(1,2,4)triazolo(1,5-a)pyrazine (Example 23, Step A) gives a protected piperazine. Removal of the t-butoxycarbonyl protecting group by treatment with acid provides the piperazine substrate for use in the coupling step.

SCHEME 4

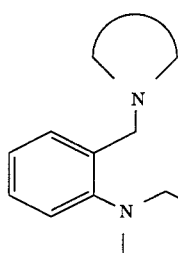

by a variety of methods, such as the procedure of Evans, D. A.; et. al. *J. Am. Chem. Soc.* 1990, 112, 4011–4030. Reduction of the oxazolidinone moiety can be carried out by a variety of metal hydride reagents (e.g. LiBH$_4$/MeOH, LiAlH$_4$, etc.). The azide is then reduced by treatment with PPh$_3$/H$_2$O or NaBH$_4$. Formation of the cyclic carbamate is accomplished by literature methods; i.e. phosgene, triphosgene or carbonyl diimidazole. The target compounds are prepared by oxidative cleavage of the olefin to the aldehyde followed by reductive amination with an amine salt as described for Scheme 1. In one method illustrated by Example 48, the aldehyde is reductively aminated with a heteroaryl substituted aryl piperazine to afford the target precursors. Hydrolysis of the cyclic carbamate under basic conditions (for example, potassium hydroxide in ethanol at elevated temperature) followed by selective amide formation at 0° C. by combining with an active acylating agent derived from an aryl carboxylic acid (for example, an aroyl chloride) gives the α-hydroxymethyl amides.

SCHEME 5

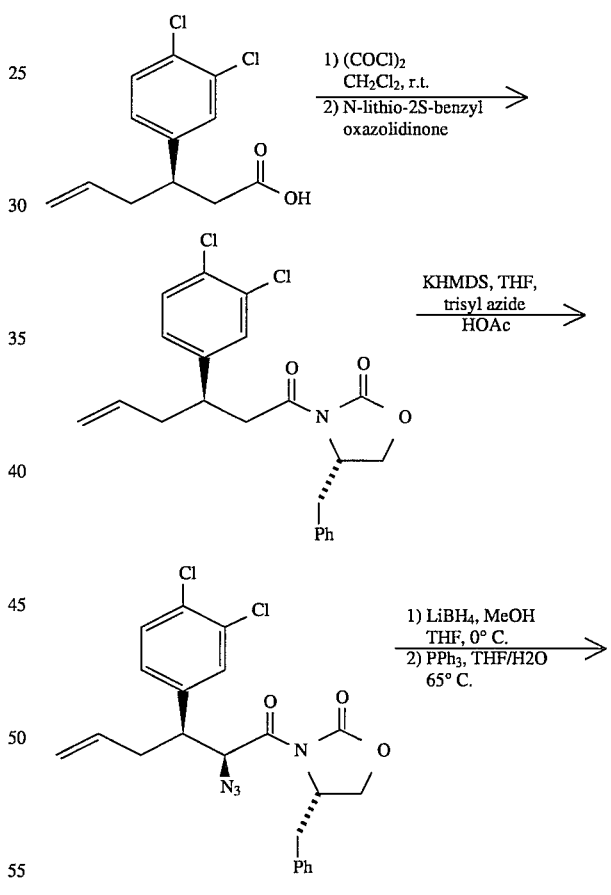

Preparation of hydroxymethyl derivatives of the target compounds is outlined in Scheme 5. The oxazolidinone imide is made from the indicated acid, by formation of the corresponding acid chloride (by treatment with oxalyl chloride or thionyl chloride) and addition of N-lithio 2(S)-benzyl oxazolidinone. The enolate azidation can be accomplished -continued
SCHEME 5

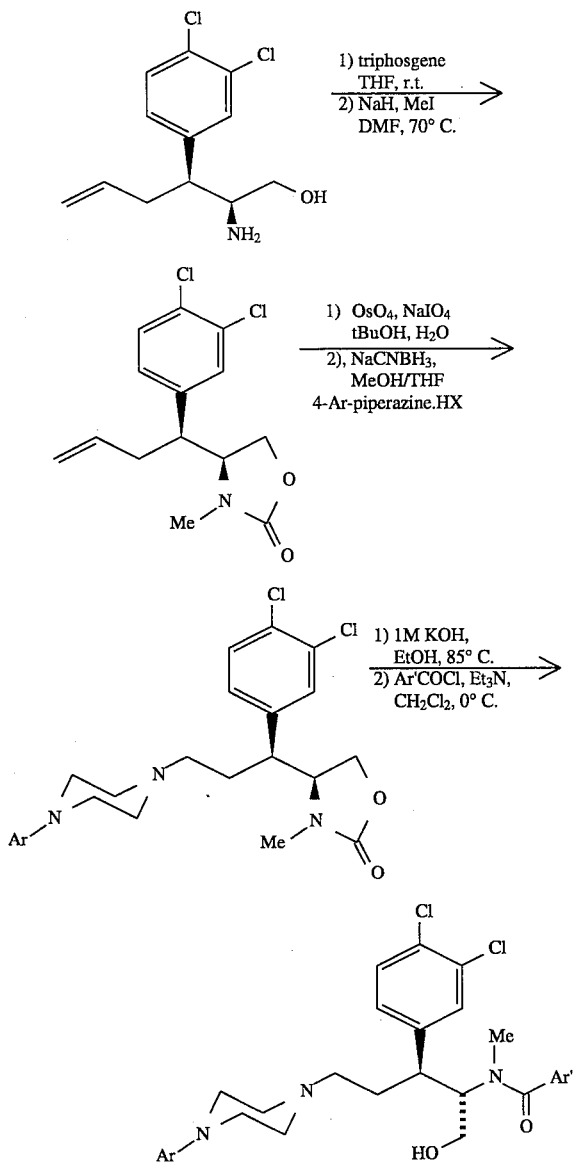

EXAMPLE 1

1-(3-((S)-(3,4-Dichlorophenyl))-4-(N-3,5-dimethylbenzoyl)-(methylamino))butyl)-4-((2-acetylaminomethyl)phenyl)-piperazine Step A: 3-((S)-(3,4-Dichlorophenyl))-4-((3,5-dimethylbenzoyl)methyl-amino)-butanal To a suspension of 4.81 g (32 mmol) of 3,5-dimethylbenzoic acid in 30 mL of CH$_2$Cl$_2$ and 7 drops of DMF was added 3.3 mL (38 mmol) of oxalyl chloride. After stirring for 1 h all the solids were dissolved and gas evolution had stopped. The solution was concentrated and the residual acid chloride was dissolved in 20 mL of CH$_2$Cl$_2$. This solution was added to a solution of 7.2 g (29 mmol) of 3-(S)-(3,4-dichlorophenyl)-4-methylamino-1-pentene (prepared as described by J. Hale et al., *Bioorganic and Medicinal Chemistry Letters*, 1993, 3, 319–322) in 50 mL of CH$_2$Cl$_2$ and 5.3 mL (38 mmol) of triethylamine (Et$_3$N) with cooling in an ice bath. The ice bath was removed after 5 min and stirring was continued for 1 h. The reaction mixture was diluted with CH$_2$Cl$_2$ and washed with water, 1.2N HCl, saturated NaHCO$_3$ and brine. The solution was dried over Na$_2$SO$_4$ and concentrated to give 11.98 g of residual oil.

$^1$H NMR (CDCl$_3$, ppm ranges are given because of amide rotamers and line broadening) 2.26 (s, 6H), 2.1–3.9 (m, 8H), 4.9–5.1 (m, 2H), 5.4–5.7 (m, 1H), 6.5–7.4 (m, 6H).

The residue was dissolved in 45 mL of acetone, 15 mL of t-butanol and 15 mL of water. To this solution 0.75 mL of osmium tetroxide (4% solution in water) and 3.63 g (31 mmol) of 4-methylmorpholine N-oxide were added. After stirring for 18 h, the reaction was quenched with approximately 30 mL of 10% aqueous Na$_2$SO$_3$ and concentrated to 25% of the original volume. The residue was partitioned between water and 1:1 ether (Et$_2$O), ethyl acetate (EtOAc), the layers were separated and the aqueous layer was reextracted with Et$_2$O:EtOAc. Each organic layer was washed with water, brine and dried by filtering through Na$_2$SO$_4$. The combined filtrate was concentrated to afford the crude diol.

A solution of the diol in 60 mL of tetrahydrofuran (THF) and 20 mL of water was treated with 6.63 g (31 mmol) of sodium periodate. After stirring for 2 h, the reaction was diluted with Et$_2$O:EtOAc and washed with water and brine. The organic layer was dried (Na$_2$SO$_4$) and the filtrate was concentrated. The residue was purified by prep LC using 30% EtOAC/hexane to furnish 7.86 g (72% yield for three steps) of the title compound as a light yellow solid.

$^1$H NMR (CDCl$_3$, ppm ranges are given because of amide rotamers and line broadening) δ 2.27 (s, 6H), 2.6–3.9 (m, 8H), 6.5–7.5 (m, 6H), 9.73 (s, 1H).

Step B: 1-t-Butoxycarbonyl-4-(2-cyano)phenyl-piperazine

To a 30 ml DMF solution of t-butylpiperazine carboxylate 10 g (53.7 mmol) and o-fluorobenzonitrile 4.34 g (35.8 mmol) were added potassium carbonate 22.26 g (161 mmol) and copper powder 230 mg (3.6 mmol). The reaction mixture was stirred at 150° C. in an oil bath overnight. After cooling to rt, the reaction mixture was concentrated reduced pressure. The residual material was suspended in EtOAc and was filtered through a pad of celite. The filtrate was washed with sat NH$_4$Cl aq. solution, dried over anhydrous Na$_2$SO$_4$, filtered, concentrated, chromatographed on silica gel column eluting with Hexanes: EtOAc=10:1 to 7:1 to give 7.84 g of the title compound.

$^1$H-NMR (400 MHz CDCl3) δ 1.46 (9H,s), 3.13 (4H, m), 3.61 (4H, m), 6.99–7.04 (2H, s), 7.46–7.58 (2H, s).

Step C: 1-t-Butoxycarbonyl-4-(2-aminomethyl)phenyl-piperazine 1-t-Butoxycarbonyl-4-(2-cyano)phenyl-piperazine 3 g (10.4 mmol) was dissolved in EtOH (65 ml) and liq. NH$_3$ (13 ml), and was hydrogenated in a bomb (H$_2$ 1000 psi, 80° C., 36 hr). The solvent was then removed under reduced pressure to give the title compound. This material was used in step D below without further purification.

Step D: 4-(2-(Acetylaminomethyl)phenyl)-piperazine

A solution of 0.258 g (0.89 mmol) of 4-(2-aminomethyl)phenyl-1-t-butoxycarbonylpiperazine (from Step C above) in 3 mL of CH$_2$Cl$_2$ was treated with 0.075 mL (1.06 mmol) of acetyl chloride and 0.15 mL (1.07 mmol) of $Et_3N$. After stirring for 20 min the reaction mixture was diluted with $CH_2Cl_2$ and washed with water, saturated $NaHCO_3$, brine and dried over $Na_2SO_4$. The filtrate was concentrated and the residue was treated with 10 drops of anisole and 2 mL of cold TFA. The solution was stirred in an ice bath for 1 hr, then concentrated. The residue was partitioned between $CH_2Cl_2$ and dilute NaOH. The organic layer was washed with brine, dried and the filtrate was concentrated to furnish 0.198 g (96%) of the title compound which was used in the next step without purification.

$^1$H NMR ($CDCl_3$) δ 2.0 (s, 3H), 2.90 (m, 4H), 3.02 (m, 4H), 4.52 (AB, 2H), 6.55 (br s, 1H), 6.85–7.4 (m, 4H).

Step E: 1-(3-((S)-(3,4-Dichlorophenyl))-4-(N-3,5-dimethylbenzoyl)(methyl-amino))butyl)-4-(2-(acetylaminomethyl)phenyl)-piperazine To a solution of 0.12 g (0.32 mmol) of 3-((S)-(3,4-dichlorophenyl))-4-((3,5-dimethylbenzoyl)methylamino)butanal (Step A) in 1 mL of MeOH were added 0.099 g (0.42 mmol) of 4-(2-acetylaminomethyl)phenyl-piperazine (Step D), 0.3 g of powdered 4 Å molecular sieves and 20 uL of acetic acid. After stirring the mixture for 1.5 h a solution of 0.063 g (1 mmol) of $NaCNBH_3$ in 3 mL of THF was added. Some gas evolution was observed. After 1 h when the reaction was complete by TLC the mixture was filtered through a pad of celite, the reaction flask and the pad were rinsed with MeOH. The filtrate was concentrated to approximately 2 mL and the residue was diluted with $Et_2O$:EtOAc. The $Et_2O$:EtOAc solution was washed with water, brine and dried over $Na_2SO_4$. The filtrate was concentrated and the residue was purified by prep TLC using 88:10:2 EtOAc:MeOH:$Et_3N$ to isolate 0.163 g (86%) of the title compound as a white foam.

$^1$H NMR ($CDCl_3$, ppm ranges are given because of amide rotamers and line broadening) δ 1.98 (s, 3H), 1.5–3.9 (m, 18H), 2.27 (s, 6H), 4.48 (AB, 2H), 6.3–6.5 (br, 1H), 6.6–7.5 (m, 10H).

EXAMPLE 2

1-(3-((S)-(3,4-Dichlorophenyl))-4-(N-3,5-dichlorobenzoyl)(methylamino))butyl)-4-(2-(acetylaminomethyl)phenyl)-piperazine Step A: 3-((S)-(3,4-Dichlorophenyl))-4-((3,5-dichlorobenzoyl)methyl-amino)-butanal The title compound was prepared following the procedures described in Example 1, Step A but using 3,5-chlorobenzoyl chloride in the place of freshly prepared 3,5-dimethylbenzoyl chloride.

$^1$H NMR ($CDCl_3$, ppm ranges are given because of amide rotamers and line broadening) δ 2.6–3.9 (m, 8H), 6.7–7.5 (m, 6H), 9.7 (s, 1H).

Step B: 1-(3-((S)-(3,4-Dichlorophenyl))-4-(N-3,5-dichlorobenzoyl)-(methylamino))butyl)-4-(2-acetylaminomethylphenyl)-piperazine The title compound was prepared by the procedure described in Example 1, Step E by substituting 3-((S)-(3,4-dichlorophenyl))-4-((3,5-dichlorobenzoyl)methylamino)butanal as the aldehyde component.

Mass Spectrum (CI) 637 ($^{37}Cl+^{35}Cl$ isotope), 635 ($^{35}Cl+^{35}Cl$ isotope).

The compounds in Examples 3–8 were prepared by reacting the requisite piperazine with either 3-((S)-(3,4-dichlorophenyl))-4-((3,5-dimethylbenzoyl)methylamino)butanal (Example 1, Step A) or 3-((S)-(3,4-dichlorophenyl))-4-((3,5-dichlorobenzoyl)methylamino)butanal (Example 2, Step A) according to the procedure of Example 1, Step E. The piperazine substrates were synthesized by the method of Example 1, Step D by substituting the appropriate acylation reagent.

EXAMPLE 3

1-(3-((S)-(3,4-Dichlorophenyl))-4-(N-3,5-dimethylbenzoyl)-(methylamino))butyl)-4-((2-methylaminocarbonylaminomethyl)phenyl)-piperazine Mass Spectrum (CI) 612 ($^{37}Cl+^{35}Cl$ isotope), 610 ($^{35}Cl+^{35}Cl$ isotope).

EXAMPLE 4

1-(3-((S)-(3,4-Dichlorophenyl))-4-(N-3,5-dimethylbenzoyl)-(methylamino))butyl)-4-((2-dimethylaminocarbonylaminomethyl)phenyl)-piperazine Mass Spectrum (CI) 626 ($^{37}Cl+^{35}Cl$ isotope), 624 ($^{35}Cl+^{35}Cl$ isotope).

EXAMPLE 5

1-(3-((S)-(3,4-Dichlorophenyl))-4-(N-3,5-dimethylbenzoyl)-(methylamino))butyl)-4-(2-methylsulfonylaminomethylphenyl)-piperazine Mass Spectrum (CI) 633 ($^{37}Cl+^{35}Cl$ isotope), 631 ($^{35}Cl+^{35}Cl$ isotope).

EXAMPLE 6

1-(3-((S)-(3,4-Dichlorophenyl))-4-(N-3,5-dichlorobenzoyl)-(methylamino))butyl)-4-((2-methylaminocarbonylaminomethyl)phenyl)-piperazine Mass Spectrum (CI) 652 ($^{37}Cl+^{35}Cl$ isotope), 650 ($^{35}Cl+^{35}Cl$ isotope).

EXAMPLE 7

1-(3-((S)-(3,4-Dichlorophenyl))-4-(N-3,5-dichlorobenzoyl)-(methylamino))butyl)-4-((2-dimethylaminocarbonylaminomethyl)phenyl)-piperazine Mass Spectrum (CI) 668 ($^{37}Cl+^{35}Cl$ isotope), 666 ($^{35}Cl+^{35}Cl$ isotope).

EXAMPLE 8

1-(3-((S)-(3,4-Dichlorophenyl))-4-(N-3,5-dichlorobenzoyl)-(methylamino))butyl)-4-(2-methylsulfonylaminomethylphenyl)-piperazine Mass Spectrum (CI) 675 ($^{37}Cl+^{35}Cl$ isotope), 673 ($^{35}Cl+^{35}Cl$ isotope).

EXAMPLE 9

1-(3-((S)-(3,4-Dichlorophenyl))-4-(N-3,5-dimethylbenzoyl)-(methylamino))butyl)-4-(2-((1'-imidazolyl)methyl)phenyl)-piperazine

Step A: 1-t-Butoxycarbonyl-4-(2-formylphenyl)-piperazine

To a solution of 1 g (8 mmol) of 2-fluorobenzaldehyde in 14 mL of DMF was added 2.25 g (12.1 mmol) of t-butyl 1-piperazinecarboxylate. The resulting solution was treated with 50 mg (0.8 mmol) of copper powder and 5.1 g (36.3 mmol) of ground $K_2CO_3$ and the suspension was heated to 150° C. in a sealed tube. After 18 h, the reaction was cooled and the contents of the tube were partitioned between water and EtOAc. The aqueous layer was reextracted with EtOAc and the organic layers were combined. The organic layer was washed with water, brine and dried. The filtrate was concentrated and the residue was chromatographed on a flash column with 12% EtOAc-Hexane to furnish 1.15 g (49%) of 1-t-butoxycarbonyl-4-(2-formylphenyl)-piperazine.

$^1$H NMR (CDCl$_3$) δ 1.44 (s, 9H), 3.0 (m, 4H), 3.59 (m, 4H), 7.0–7.8 (m, 4H), 10.31 (s, 1H).

Step B: 1-t-Butoxycarbonyl-4-(2-hydroxymethylphenyl)-piperazine

A solution of 1.15 g (3.96 mmol) of 1-t-butoxycarbonyl-4-(2-formyl-phenyl)-piperazine in 10 mL of MeOH was treated with 0.15 g (3.96 mmol) of NaBH$_4$. After 2 h the reaction was quenched by adding 1.2N HCl and the mixture was extracted with EtOAc. The EtOAc solution was washed with water, brine and dried. The filtrate was concentrated to yield 1.1 g (95%) of 1-t-butoxycarbonyl-4-(2-hydroxymethyl-phenyl)-piperazine as a white foam which was used without purification.

$^1$H NMR (CDCl$_3$) δ 1.24 (s, 9H), 2.92 (m, 4H), 3.59 (m, 4H), 4.84 (s, 2H), 7.0–7.4 (m, 4H).

Step C: 1-t-Butoxycarbonyl-4-(2-((1'-imidazolyl)methyl)phenyl)-piperazine

To 0.2 g (0.68 mmol) of 1-t-butoxycarbonyl-4-(2-hydroxymethylphenyl)-piperazine in 2 mL of CH$_2$Cl$_2$ were added 0.064 mL (0.82 mmol) of methanesulfonyl chloride and 0.11 mL (0.82 mmol) of Et$_3$N. After stirring for 30 min the reaction was partitioned between water and CH$_2$Cl$_2$. The CH$_2$Cl$_2$ layer was washed with brine, dried and concentrated and the residue was dissolved in 1 mL of DMF. This solution was added to a mixture of 51 mg (0.75 mmol) of imidazole in 1 mL of DMF and 18 mg (0.75 mmol) of NaH which had been stirred for 30 min. After heating the reaction mixture for 18 h at 60° C., it was cooled and partitioned between water and EtOAc. The organic layer was washed with water, brine, dried and the filtrate was concentrated. The residue was chromatographed using 5% MeOH—CH$_2$Cl$_2$ to isolate 0.096 g (41%) of 1-t-butoxycarbonyl-4-(2-((1'-imidazolyl)methyl)phenyl)-piperazine.

$^1$H NMR (CDCl$_3$) δ 1.46 (s, 9H), 2.74 (m, 4H), 3.53 (m, 4H), 5.2 (s, 2H) 6.89 (s, 1H), 7.0–7.4 (m, 5H), 7.54 (s, 1H).

Step D: 4-(2-((1'-Imidazolyl)methyl)phenyl)-piperazine

Cold TFA (1 mL) and 0.1 mL of anisole were added to 0.096 g (0.28 mmol) of 1-t-butoxycarbonyl-4-(2-((1'-imidazolyl)methyl)phenyl)-piperazine. The bath was removed and the mixture stirred for 1 h while it warmed to room temperature. The reaction mixture was concentrated and the residue was partitioned between CH$_2$Cl$_2$ and dilute NaOH. The CH$_2$Cl$_2$ layer was washed with brine, dried and concentrated to give 0.047 g (69%) of the title compound which was used without purification.

$^1$H NMR (CDCl$_3$) δ 2.78 (m, 4H), 3.02 (m, 4H), 5.2 (s, 2H), 6.89–7.4 (m, 6H), 7.54 (s, 1H).

Step E: 1-(3-((S)-(3,4-Dichlorophenyl))-4-(N-3,5-dimethylbenzoyl(methylamino))butyl)-4-(2-((1'-imidazolyl)methyl)-phenyl)-piperazine A reaction between 47 mg (0.19 mmol) of 4-(2-((1'-imidazolyl)methyl)phenyl)-piperazine and 92 mg (0.24 mmol) of 3-((S)-(3,4-dichlorophenyl))-4-((3,5-dimethylbenzoyl)methylamino)butanal according to the method of Example 1, Step E furnished 55 mg (47%) of the title compound.

$^1$H NMR (CDCl$_3$, ppm ranges are given because of amide rotamers and line broadening) δ 1.5–3.9 (m, 18H), 2.27 (s, 6H), 5.14 (s, 2H), 6.6–7.6 (m, 13H).

Mass Spectrum (CI) 606 ($^{37}$Cl+$^{35}$Cl isotope), 604 ($^{35}$Cl+$^{35}$Cl isotope).

The compounds in Examples 10–14 were prepared by the procedure of Example 9 substituting the requisite heterocycle for imidazole in Step C and carrying out Step E with either 3-((S)-(3,4-dichlorophenyl))-4-((3,5-dimethylbenzoyl)methyl-amino)-butanal (from Example 1, Step A) or 3-((S)-(3,4-dichlorophenyl))-4-((3,5-dichlorobenzoyl)methyl-amino)-butanal (from Example 2, Step A).

EXAMPLE 10

1-(3-((S)-(3,4-Dichlorophenyl))-4-(N-3,5-dichlorobenzoyl)-(methylamino))butyl)-4-(2-(1'-(1',2',4'-triazolyl)methylphenyl)-piperazine Mass Spectrum (CI) 647 ($^{37}$Cl+$^{35}$Cl isotope), 645 ($^{35}$Cl+$^{35}$Cl isotope).

EXAMPLE 11

1-(3-((S)-(3,4-Dichlorophenyl))-4-(N-3,5-dimethylbenzoyl)-(methylamino))butyl-4-(2-(1'-(1',2',4'-triazolyl)methylphenyl)-piperazine Mass Spectrum (CI) 607 ($^{37}$Cl+$^{35}$Cl isotope), 605 ($^{35}$Cl+$^{35}$Cl isotope).

EXAMPLE 12

1-(3-((S)-(3,4-Dichlorophenyl))-4-(N-3,5-dimethylbenzoyl)-(methylamino))butyl)-4-(2-(1'-(1',2',3',4'-tetrazolyl)methylphenyl)-piperazine Mass Spectrum (CI) 608 ($^{37}$Cl+$^{35}$Cl isotope), 606 ($^{35}$Cl+$^{35}$Cl isotope).

EXAMPLE 13

1-(3-((S)-(3,4-Dichlorophenyl))-4-(N-3,5-dimethylbenzoyl)-(methylamino))butyl)-4-(2-(3'-pyridyloxy)methylphenyl)-piperazine The title compound was synthesized by the method of Example 9 by substituting 3-hydroxypyridine for imidazole in Step C.

Mass Spectrum (CI) 633 ($^{37}$Cl+$^{35}$Cl isotope), 631 ($^{35}$Cl+ $^{35}$Cl isotope).

EXAMPLE 14

1-(3-((S)-(3,4-Dichlorophenyl))-4-(N-3,5-dimethylbenzoyl)-(methylamino))butyl)-4-(2-(1'-(2'(1'H)-pyridone)methylphenyl)-piperazine The title compound was prepared according to Example 9 and using 2-hydroxypyridine in Step C.

Mass Spectrum (CI) 633 ($^{37}$Cl+$^{35}$Cl isotope), 631 ($^{35}$Cl+ $^{35}$Cl isotope).

EXAMPLE 15

1-(3-((S)-(3,4-Dichlorophenyl))-4-(N-(3,5-dimethylbenzoyl)-(methylamino))butyl)-4-(2-methylphenyl)-piperazine

Step A: 3-(S)-(3,4-Dichlorophenyl)-4-(N-(3,5-dimethylbenzoyl)methylamino)butanol To a solution of 3-((S)-(3,4-dichlorophenyl)-4-(N-(3,5-dimethylbenzoyl)methylamino)butanal (2.5 g; from Example 1, Step A) in 35 mL of methanol at 0° C. was added portionwise over 5 min sodium borohydride (400 mg). After stirring for 1 h at r.t., the reaction was slowly quenched with 2N HCl and extracted twice with ethyl acetate. The organic layers were washed with brine, dried (Na$_2$SO$_4$), combined and evaporated to give 2.5 g (100%) of a crude oil. Residual water and methanol were removed by concentration from a portion of isopropyl acetate.

Step B: 4-Bromo-2-(S)-(3,4-dichlorophenyl)-1-(N-(3,5-dimethylbenzoyl)methylamino)butane To a solution of crude 3-(S)-(3,4-dichlorophenyl)-4-(N-(3,5-dimethylbenzoyl)methylamino)butanol (2.5 gm) from Step A in 30 mL of acetonitrile was added 3.5 g (8.25 mmol) of triphenylphoshine dibromide. The reaction was stirred at r.t. for 16 h and was then partitioned between ethyl ether and water. The organic layer was washed with brine, dried (Na$_2$SO$_4$) and concentrated. The residue was flash chromatograghed with a solvent gradient of 25–40% EtOAc/Hexanes to give 2.6 g (89% from Step A) of oil which solidified on standing.

Mass Spectrum (ESI 80/20MeCN/H$_2$O, 0.01% TFA) M+H=441, 443, 445 ($^{35,37}$Cl, $^{79}$Br, $^{81}$Br-isotope).

Step C: (3-((S)-(3,4-Dichlorophenyl))-4-(N-(3,5-dimethylbenzoyl)(methyl-amino))butyl)-4-(2-methylphenyl)-piperazine A solution of 4-bromo-2-(S)-(3,4-dichlorophenyl)-1-(N-(3,5-dimethylbenzoyl)methylamino)butane prepared in Step B (50 mg), N,N-diisopropylethylamine (40 ul) and 1-(2-methylphenyl)-piperazine (40 mg) in 0.5 mL of acetonitrile was heated in a tightly capped vial at 50° C. for four days. The solvent was evaporated and the residue was purified on a 1000 um silica gel prep plate (4% MeOH/CH$_2$Cl$_2$)) to furnish 30 mg (50%) of the title compound as a white foam.

Mass Spectrum (CI/NH$_3$) M+H=537, 539 ($^{35,37}$Cl-isotope).

EXAMPLE 16

1-(3-((S)-(3,4-Dichlorophenyl))-4-(N-(3,5-dimethylbenzoyl)-(methylamino))butyl)-4-(phenyl)piperazine Following essentially the same procedure as in Example 15 but substituting 1-phenylpiperazine (35 mg), 30 mg (51%) of the title compound was prepared.

Mass Spectrum (CI/NH$_3$) M+H=523, 525 ($^{35,37}$Cl-isotope).

EXAMPLE 17

1-(3-((S)-(3,4-Dichlorophenyl))-4-(N-(3,5-dimethylbenzoyl)-(methylamino))butyl)-4-(9-(2-fluoroethyl)-2-methoxy-purin-6-yl)piperazine A mixture of 4-bromo-2-(S)-(3,4-dichlorophenyl)-1-(N-(3,5-dimethylbenzoyl)methylamino)butane prepared in Example 15, Step B above (43.5 mg), N,N-diisopropylethylamine (68 ul) and 9-(2-fluoroethyl)-2-methoxy-6-(1-piperazinyl)purine dihydrochloride (69 mg; prepared according to D. B. Johnston, M. MacCoss, S. Marburg, L. Meurer, and R. L. Tolman; U.S. Pat. No. 5,057,517) in 0.5 mL of acetonitrile was heated in a tightly capped vial at 50° C. for four days. The solvent was evaporated and the residue was purified on a 1000 um silica gel prep plate (93:5:2 ethyl acetate:methanol:triethylamine) to furnish 32.5 mg of the title compound as a white foam.

Mass Spectrum (CI/NH$_3$) M+H=642, 644 ($^{35,37}$Cl-isotope).

The compounds in Examples 18–30 were (unless otherwise stated) prepared from 4-bromo-2-(S)-(3,4-dichlorophenyl)-1-(N-(3,5-dimethylbenzoyl)methylamino)butane (prepared in Example 15, Step B) and the appropiate piperazine derivatives by essentially the same procedure as in Example 17.

EXAMPLE 18

1-(3-((S)-(3,4-Dichlorophenyl))-4-(N-(3,5-dimethylbenzoyl)(methylamino))butyl)-4-(9-(2-methoxymethyl)-2-methoxy-purin-6-yl)piperazine The starting piperazine was prepared according to D. B. Johnston, M. MacCoss, S. Marburg, L. Meurer, and R. L. Tolman; U.S. Pat. No. 5,057,517.

Mass Spectrum (CI/NH$_3$) M+H=640, 642 ($^{35,37}$Cl-isotope).

EXAMPLE 19

1-(3-((S)-(3,4-Dichlorophenyl))-4-(N-(3,5-dimethylbenzoyl)(methylamino))butyl)-4-(9-methyl-purin-6-yl)piperazine The starting piperazine was prepared according to D. B. Johnston, M. MacCoss, S. Marburg, L. Meurer, and R. L. Tolman; U.S. Pat. No. 5,057,517.

Mass Spectrum (CI/NH$_3$) M+H=580, 582 ($^{35,37}$Cl-isotope).

EXAMPLE 20

1-(3-((S)-(4-Chlorophenyl))-4-(N-(3,5-dimethylbenzoyl)(methylamino))butyl)-4-(9-methyl-purin-6-yl)piperazine The title compound was prepared from 4-bromo-2-(S)-(4-chlorophenyl)-1-(N-(3,5-dimethylbenzoyl)methylamino)butane (prepared by analogy to 4-bromo-2-(S)-(3,4-dichlorophenyl)-1-(N-(3,5-dimethylbenzoyl)methylamino)butane in Example 15, Steps A and B) and the requisite piperazine, which was prepared according to D. B. Johnston, M. MacCoss, S. Marburg, L. Meurer, and R. L. Tolman; U.S. Pat. No. 5,057,517.

Mass Spectrum (CI/NH$_3$) M+H=546, 548 ($^{35,37}$Cl-isotope).

EXAMPLE 21

1-(3-((S)-(3,4-Dichlorophenyl))-4-(N-(3,5-dimethylbenzoyl)(methylamino))butyl)-4-(6-methyl-imidazo(1,2-a)pyrazin-1-yl)piperazine The starting piperazine was prepared according to L. C. Meurer, R. L. Tolman, E. W. Chapin, R. Saperstein, P. P. Vicario, M. F. Zrada and M. MacCoss, *J. Med. Chem.* 1992, 35, 3845–3857.

Mass Spectrum (CI/NH$_3$) M+H=579, 581 ($^{35,37}$Cl-isotope).

EXAMPLE 22

1-(3-((S)-(3,4-Dichlorophenyl))-4-(N-(3,5-dimethylbenzoyl)(methylamino))butyl)-4-(1,7-naphthyridin-8-yl)piperazine Step A: 8-(1-(4-t-Butyloxycarbonyl)piperazinyl)-1,7-naphthyridine To a solution of 1.56 g (9.48 mml) of 8-chloro-1,7-naphthyridine (*J. Org. Chem.* 1963, 28, 1753) in 100 mL of isoamyl alcohol was added 1-(t-butyloxycarbonyl)piperazine (6.36 g, 34.15 mmol). This solution was heated under reflux, under nitrogen for 2 hr and then the reaction mixture was evaporated to dryness and the residue was dissolved in CH$_2$Cl$_2$ (100 mL) and 10% aq. Na$_2$CO$_3$ (100 mL). After shaking, the layers were separated and the aqueous layer was washed with CH$_2$Cl$_2$ (2×100 mL) and the pooled organic layers were dried (over MgSO$_4$), filtered, and evaporated to dryness. This oily residue was dissolved in a little CH$_2$Cl$_2$, absorbed onto silica gel 60, and chromatographed on a dry-packed silica gel 60 column (3.5×20.5 cm) developed with EtOAc: hexanes (1:3). Fractions containing the desired product were pooled and evaporated to dryness to give a thick yellow syrup which crystallized on standing. Yield 2.78 g (8.84 mmol, 93% yield).

Mass Spec. showed M$^+$ at m/e 314.

Analysis calculated for C$_{17}$H$_{22}$N$_4$O$_2$ (314) C, 64.95; H, 7.05; N, 17.82 Found: C, 64.53; H, 6.71; N, 17.66

Step B: 8-(1-Piperazinyl)-1,7-naphthyridine dihydrochloride 8-(1-(4-t-Butyloxycarbonyl)piperazinyl)-1,7-naphthyridine, prepared as described above (1.02 g, 3.24 mmol), was dissolved in abs. EtOH (10 mL) and ethanolic HCl (8 mL) was added. This solution was left at room temperature for 10 min and then was evaporated to dryness slowly under a nitrogen stream. This residue was evaporated to dryness from H$_2$O and then from EtOH to give a white residue that was triturated under EtOH, filtered, and dried at 45° C. in vacuo to give 0.71 g (2.47 mmol, 76% yield) of the title compound.

Analysis calculated for C$_{12}$H$_{16}$N$_4$Cl$_2$ (287.19) C, 50.19; H, 5.62; N, 19.51 Found: C, 49.89; H, 5.51; N, 19.28

Step C: 1-(3-((S)-(3,4-Dichlorophenyl))-4-(N-(3,5-dimethylbenzoyl)(methylamino))butyl)-4-(1,7-naphthyridin-8-yl)piperazine The title compound was prepared by reacting 4-bromo-2-(S)-(3,4-dichlorophenyl)-1-(N-(3,5-dimethylbenzoyl)methylamino)butane and 8-(1-piperazinyl)-1,7-naphthyridine dihydrochloride according to the procedure of Example 17.

Mass Spectrum (CI/NH$_3$) M+H=576, 578 ($^{35,37}$Cl-isotope).

EXAMPLE 23

1-(3-((S)-(3,4-Dichlorophenyl))-4-(N-(3,5-dimethylbenzoyl)(methylamino))butyl)-4-(1,2,4-triazolo(1.5-a)pyrazin-8-yl)piperazine Step A: 8-(1-(4-t-Butyloxycarbonyl)piperazinyl)-(1,2,4)-triazolo(1.5-a)pyrazine 8-Chloro-(1,2,4)-triazolo(1,5-a)pyrazine (*J. Org. Chem,* 1974, 39, 2143 and *J.C.S. Perkin I,* 1980, 506) (1.62 g, 10.41 mmol) and 1-(t-butyloxycarbonyl)piperazine (8.15 g, 43.76 mmol, prepared as described in *J. Het. Chem.* 1990 27, 1559) were mixed and dissolved in EtOH (75 mL). This solution was heated under reflux, under nitrogen, for 2 hr and then the mixture was evaporated to dryness under reduced pressure and the residue was dissolved in i-pentyl alcohol (75 mL) and the reflux continued for 4 hr. The reaction mixture was cooled and evaporated to dryness to give a yellow syrupy residue that was dissolved in CH$_2$Cl$_2$ (60 mL) and 10% aq. Na$_2$CO$_3$ (60 mL). After shaking, the layers were separated and the aqueous layer was washed with CH$_2$Cl$_2$ (2×60 mL) and the pooled organic layers were dried (over MgSO$_4$), filtered, and evaporated to dryness. The residue was dissolved in a little CH$_2$C$_{12}$, absorbed onto silica gel 60, and chromatographed on a dry-packed silica gel 60 column (3×36 cm) developed with EtOAc:hexanes (1:3). Fractions containing the required product were pooled and evaporated to dryness to give 2.15 g (7.04 mmol, 67% yield) of the title compound.

Mass Spec. showed M$^+$ at m/e 304.

Analysis calculated for C$_{14}$H$_{20}$N$_6$O$_2$ (304.35) C, 55.25; H, 6.62; N, 27.61 Found: C, 55.18; H, 6.53; N, 27.30

Step B: 8-(1-Piperazinyl)-(1,2,4)-triazolo(1,5-a)pyrazine dihydrochloride 8-(1-(4-t-Butyloxycarbonyl)piperazinyl)-(1,2,4)-triazolo(1,5-a)pyrazine (1.18 g, 3.86 mmol), was dissolved in EtOH:EtOAc (1:1, 40 mL) with warming and ethanolic HCl (10 mL) was added. Precipitation occurred immediately and the mixture was left at room temperature for 2½ hr. The reaction mixture was blown down to dryness under a nitrogen stream and triturated under EtOH/EtOAc/Et$_2$O and the whim solid so obtained was filtered off and dissolved in CF$_3$CO$_2$H (15 mL) and then evaporated under a stream of nitrogen over a period of 1½ hr. The residue so obtained was evaporated to dryness twice from H$_2$O and then dissolved in a little H₂O and passed down a Dowex 1×2 (OH⁻ form) column (2×26 cm) packed and developed in H₂O. Fractions containing the required product were pooled and evaporated to dryness to give 0.78 g (3.82 mmol, 99% yield) of the title compound as the free base. This was dissolved in EtOH (15 mL) with warming and ethanolic HCl was added. Immediate precipitation of the product occurred and this was filtered off after dilution with Et₂O to give 1.00 g (3.61 mmol, 94% yield overall) of the title compound.

Analysis calculated for $C_9H_{14}N_6Cl_2 \cdot 0.5H_2O$ (286.15) C, 37.77; H, 5.28; N, 29.37 Found: C, 37.63; H, 5.28; N, 29.23

Step C: 1-(3-((S)-(3,4-Dichlorophenyl))-4-(N-(3,5-dimethylbenzoyl)-(methylamino))butyl)-4-(1,2,4-triazolo(1,5-a)pyrazin-8-yl)piperazine Reaction of 4-bromo-2-(S)-(3,4-dichlorophenyl)-1-(N-(3,5-dimethylbenzoyl)methylamino)butane with 8-(1-piperazinyl)-(1,2,4)-triazolo(1,5-a)pyrazine dihydrochloride as described in example 17 gave the title compound.

Mass Spectrum (CI/NH₃) M+H=566, 568 ($^{35,37}$Cl-isotope).

EXAMPLE 24

1-(3-((S)-(3,4-Dichlorophenyl))-4-(N-(3,5-dimethylbenzoyl)(methylamino))butyl)-4-(5-methyl-pyrid-2-yl)piperazine The starting piperazine was prepared according to U.S. Pat. No. 4,876,256 (1989).

Mass Spectrum (CI/NH₃) M+H=539, 541 ($^{35,37}$Cl-isotope).

EXAMPLE 25

1-(3-((S)-(3,4-Dichlorophenyl))-4-(N-(3,5-dimethylbenzoyl)-(methylamino))butyl)-4-(2-amino-pyrazin-4-yl)piperazine Step A: 2-Amino-4-(1-piperazinyl)pyrimidine dihydrochloride 2-Amino-6-chloro-4-(1-piperazinyl)pyrimidine, prepared as described in *J. Med. Pharm. Chem.*, 5, 558 (1962), (1.07 g, 5 mmol) was suspended in EtOH (100 mL) and heated and sonicated to effect maximum dissolution. MgO (0.75 g) was added followed by 5% Pd on C (0.48 g). The mixture was hydrogenated for 18¾ hr at room temperature and then was warmed and filtered while hot through a Celite pad, washing the pad well with hot EtOH. The filtrate was evaporated to a white solid residue (1.14 g, quantitative yield). An analytical sample was obtained by conversion to the dihydrochloride salt using ethanolic HCl in the usual fashion.

Anal. Calc. for $C_8H_{15}N_5Cl_2 \cdot 0.1H_2O$ (253.94): C 37.84; H 6.03; N 27.58; Cl 27.92 Found: C 38.21; H 5.90; N 27.15; Cl 28.02

Step B: 1-(3-((S)-(3,4-Dichlorophenyl))-4-(N-(3,5-dimethylbenzoyl)-(methylamino))butyl)-4-(2-aminopyrazin-4-yl)piperazine Reaction of 4-bromo-2-(S)-(3,4-dichlorophenyl)-1-(N-(3,5-dimethylbenzoyl)methylamino)butane with 2-amino-4-(1-piperazinyl)pyrimidine dihydrochloride according to the procedure given in Example 17 gave the title compound.

Mass Spectrum (CI/NH₃) M+H=541, 543 ($^{35,37}$Cl-isotope).

EXAMPLE 26

1-(3-((S)-(3,4-Dichlorophenyl))-4-(N-(3,5-dimethylbenzoyl)-(methylamino))butyl)-4-(furo(2,3-c)pyrid-4-yl))piperazine Step A: 7-(1-(4-t-Butyloxycarbonyl)piperazinyl)furo(2,3-c)pyridine 7-Chlorofuro(2,3-c)pyridine, prepared as described in *J. Heterocyclic Chem.*, 19, 1207 (1982), (1.54 g, 10 mmol) and 1-(t-butyloxycarbonyl)piperazine (7.45 g, 40 mmol) were mixed and heated at 180° C. under nitrogen for 3 hr, cooled, and the residue was partitioned between CHCl₃ (50 mL) and 5% aqueous NaHCO₃ (30 mL). The organic phase was dried and evaporated to dryness and the oil so obtained was dissolved in CHCl₃ and chromatographed on a column of silica gel, developed initially with CHCl₃ and then with hexanes:EtOAc (3:1). Fractions containing the required product were pooled and evaporated to dryness to give 1.90 g of the title compound.

anal. Calc. for $C_{14}H_{22}N_4O_3$ (294.36): C 57.12; H 7.53; N 19.03 Found: C 56.77; H 7.24; N 19.16

Step B: 7-(Piperazinyl)furo(2,3-c)pyridine trifluoroacetate

The title compound was prepared by deprotection of 7-(1-(4-t-butyloxycarbonyl)piperazinyl)furo(2,3-c)pyridine with trifluoroacetic acid in methylene chloride in the presence of anisole. The crude product was used immediately in Step C.

Step C: 1-(3-((S)-(3,4-Dichlorophenyl))-4-(N-(3,5-dimethylbenzoyl)-(methylamino))butyl)-4-(furo(2,3-c)pyrid-4-yl))piperazine Reaction of 4-bromo-2-(S)-(3,4-dichlorophenyl)-1-(N-(3,5-dimethylbenzoyl)methylamino)butane with 7-(piperazinyl)furo(2,3-c)pyridine trifluoroacetate according to the procedure given in example 17 gave the title compound.

Mass Spectrum (CI/NH₃) M+H=565, 567 ($^{35,37}$Cl-isotope).

EXAMPLE 27

1-(3-((S)-(3,4- Dichlorophenyl))-4-(N-(3,5-dimethylbenzoyl)-(methylamino))butyl)-4-(2-amino-7,8-dihydro-6H-thiopyrano(3,2-d)pyrimid-4-yl)piperazine The starting piperazine was prepared according to Kunch, Y., Iguchi, A., Gotch, M., Nomura, T., Shibata, M., Sakamoto, N. *Arch. Int. Pharmacodyn.* 1986, 280, 302–313.

Mass Spectrum (CI/NH₃) M+H=613, 615 ($^{35,37}$Cl-isotope).

EXAMPLE 28

1-(3-((S)-(3,4-Dichlorophenyl))-4-(N-(3,5-dimethylbenzoyl)-(methylamino))butyl)-4-(2-methyl-7,8-dihydro-6H-thiopyrano(3,2-d)pyrimid-4-yl)piperazine The title compound was prepared by reaction of 4-bromo-2-(S)-(3,4-dichlorophenyl)-1-(N-(3,5-dimethylbenzoyl)methylamino)butane (Example 15, Steps A and B) and 2-methyl-7,8-dihydro-4-piperazinyl-6H-thiopyrano[3,2-d]pyrimidine (prepared by analogy to the preparation of 2-amino-7,8-dihydro-4-piperazinyl-6H-thiopyrano[3,2-d]pyrimidine, as described in Ohno et al, UK Patent Application GB 2,119,368 A, 16 Nov. 1983, by substituting acetamidine hydrochloride for guanidine carbonate in the reaction with ethyl 3-oxotetrahydrothiapyran-2-carboxylate) according to the procedure given in Example 17.

Mass Spectrum (CI/NH$_3$) M+H=612, 614 ($^{35,37}$Cl-isotope).

EXAMPLE 29

1-(3-((S)-(3,4-Dichlorophenyl))-4-(N-(3,5-bis(trifluoromethyl)benzoyl)-(methylamino))butyl)-4-(1,2,4-triazolo(1,5-a)pyrazin-8-yl)piperazine The title compound was prepared by reaction of 4-bromo-2-(S)-(3,4-dichlorophenyl)-1-(N-(3,5-bis(trifluoromethyl)benzoyl)methylamino)butane (prepared by analogy to 4-bromo-2-(S)-(3,4-dichlorophenyl)-1-(N-(3,5-dimethylbenzoyl)methylamino)butane in Example 15, Steps A and B) and 8-(1-piperazinyl)-(1,2,4)-triazolo(1,5-a)pyrazine dihydrochloride (prepared in Example 23, Step B) according to the procedure given in Example 17.

Mass Spectrum (CI/NH$_3$) M+H=674.

EXAMPLE 30

1-(3-((S)-(4-Chlorophenyl))-4-(N-(3,5-bis(trifluoromethyl)benzoyl)-(methylamino))butyl)-4-(1,2,4-triazolo(1,5-a)pyrazin-8-yl)piperazine The title compound was prepared by reaction of 4-bromo-2-(S)-(4-chlorophenyl)-1-(N-(3,5-bis(trifluoromethyl)benzoyl)methylamino)butane (prepared by analogy to 4-bromo-2-(S)-(3,4-dichlorophenyl)-1-(N-(3,5-dimethylbenzoyl)methylamino)butane in Example 15, Steps A and B) and 8-(1-piperazinyl)-(1,2,4)-triazolo(1,5-a)pyrazine dihydrochloride (prepared in Example 23, Step B) according to the procedure given in Example 17.

Mass Spectrum (CI/NH$_3$) M+H=640.

EXAMPLE 31

1-(3-((S)-(3,4-Dichlorophenyl))-4-(N-(3,5-dimethylbenzoyl)-(methylamino))butyl)-4-(2-amino-7,8-dihydro-6H-thiopyrano(3,2-d)pyrimid-4-yl)piperazine-5-oxide A solution of 1-(3-((S)-(3,4-dichlorophenyl))-4-(N-(3,5-dimethylbenzoyl)-(methylamino))butyl)-4-(2-amino-7,8-dihydro-6H-thiopyrano(3,2-d)pyrimid-4-yl)piperazine (13 mg; Example 27) in 0.5 mL of methanol at 0° C. was treated with a solution of 17 mg of oxone in 0.5 mL of water. After three minutes the reaction was quenched with 10% aqueous sodium bisulfite and stirred for five minutes. The mixture was diluted with saturated sodium bicarbonate and extracted twice with dichloromethane. The combined organic layer was washed with brine, dried (Na$_2$SO$_4$) and evaporated to a clear oil. Purification on a 1000 um silica gel prep plate (9:1 CH$_2$Cl$_2$:MeOH) provided 4.6 mg of product as a white foam.

Mass Spectrum (CI/NH$_3$) M+H=629, 631 ($^{35,37}$Cl-isotope).

EXAMPLE 32

1-(3-((S)-(3,4-Dichlorophenyl))-4-(N-(3,5-dimethylbenzoyl)-(methylamino))butyl)-4-(2-methyl-7,8-dihydro-6H-thiopyrano(3,2-d)pyrimid-4-yl)piperazine-5-oxide The title compound was prepared by following essentially the same procedure as in Example 31 but employing 1-(3-((S)-(3,4-dichlorophenyl))-4-(N-(3,5-dimethyl-benzoyl)-(methylamino))butyl)-4-(2-methyl-7,8-dihydro-6H-thiopyrano(3,2-d)pyrimid-4-yl)piperazine (from Example 28) as starting material.

Mass Spectrum (CI/NH$_3$) M+H=628, 630 ($^{35,37}$Cl-isotope).

EXAMPLE 33

1-(3-((S)-(3,4-Dichlorophenyl))-4-(N-3,5-bis(trifluoromethyl)benzoyl(methylamino))butyl)-4-(2-(2'-(tetrazolyl)methyl)phenyl)-piperazine

Step A: 3-((S)-(3,4-Dichlorophenyl))-4-((N-3,5-bis-trifluoromethylbenzoyl)methylamino)-butanal Following the procedure described in Example 1 step A, 3-((S)-(3,4-dichlorophenyl))-4-((N-3,5-bis-trifluoromethylbenzoyl)methylamino)-butanal was prepared using 3,5-bis-trifluoromethylbenzoic acid instead of 3,5-dimethylbenzoic acid.

$^1$H-NMR (500 MHz CDCl$_3$) δ 2.5–4.0 (8H, m), 6.7–8.0 (6H, m), 9.78 (1H, s).

Step B: 1-t-Butoxycarbonyl-4-(2-bromomethyl)phenyl)-piperazine

To 410 mg (1.4 mmol) of 1-t-butoxycarbonyl-4-(2-hydroxymethyl)phenyl)-piperazine (prepared in Example 9, Step B) in 12 mL of acetonitrile was added 625 mg (2.38 mmol) of triphenylphosphine and 698 mg (2.1 mmol) of carbon tetrabromide with cooling in an ice-water bath. After the mixture was stirred in a cold room (4° C.) for 14 hr, the solvent was removed under reduced pressure. The resulting oil was dissolved in EtOAc and water was then added. The phases were separated and the aqueous phase was extracted with two small portions of EtOAc. The combined organic phases were dried over anhydrous Na$_2$SO$_4$, filtered, concentrated, and triturated with hexane. The triphenylphosphine oxide which precipitated was removed by filtration. The filtrate was concentrated to give the title compound, which was used in step C without further purification.

$^1$H-NMR (500 MHz CDCl$_3$) δ 1.51 (9H. s), 2.94 (4H, m), 3.61 (4H, s), 4.72 (2H, s), 7.1–7.5 (4H, m).

Step C: 1-t-Butoxycarbonyl-4-(2-(1'-(tetrazolyl)methyl)phenyl)-piperazine and

1-t-Butoxycarbonyl-4-(2-(2'-(tetrazolyl)methyl)phenyl)-piperazine

To a solution of 294 mg (4.2 mmol) of 1H-tetrazole in 9 ml DMF was added 111 mg (4.63 mmol) sodium hydride at rt. After stirring for 10 min, 9 ml of the DMF solution of 1-t-butoxycarbonyl-4-(2-bromomethyl)phenyl)-piperazine prepared in step B was added, and the mixture was stirred in an oil bath at 70° C. for 1.5 hr. The DMF was then removed under reduced pressure. The resulting material was dissolved in EtOAc and sat. NH$_4$Cl aq. solution. The organic phase was separated and the aqueous phase was extracted twice with small portions of EtOAc. The combined organic phases were dried over anhydrous Na$_2$SO$_4$, filtered, concentrated, and chromatographed on silica gel eluting with Hexane:EtOAc=5:1 to 1:1 to give 144.3 mg of 1-t-butoxycarbonyl-4-(2-(2'-(tetrazolyl)methyl)phenyl)-piperazine (higher Rf), and 224.1 mg of 1-t-butoxycarbonyl-4-(2-(1'-(tetrazolyl)methyl)phenyl)-piperazine (lower Rf).

1-t-Butoxycarbonyl-4-(2-(2'-(tetrazolyl)methyl)phenyl)-piperazine $^1$H-NMR (500 MHz CDCl$_3$) δ 1.50 (9H, s), 2.83 (4H, s), 3.58 (4H, s), 6.00 (2H, s), 7.1–7.4 (4H, m), 8.52 (1H, s).
Mass Spectrum (CI) 345 (M$^+$+1)

1-t-Butoxycarbonyl-4-(2-(1'-(tetrazolyl)methyl)phenyl)-piperazine $^1$H-NMR (500 MHz CDCl$_3$) δ 1.50 (9H, s), 2.80 (4H, s), 3.55 (4H, s), 5.73 (2H, s), 7.1–7.43 (4H, m), 8.52 (1H, s).
Mass Spectrum (CI) 245 (M$^+$+H-Boc)

Step D: 1-(3-((S)-(3,4-Dichlorophenyl))-4-(N-3,5-bis-(trifluoromethyl)benzoyl(methylamino))butyl)-4-(2-(2'-(tetrazolyl)methyl)phenyl)-piperazine 1-t-Butoxycarbonyl-4-(2-(2'-(tetrazolyl)methyl)phenyl)-piperazine was deprotected under the conditions given in Example 9, Step D, and the product was then reacted with 4-bromo-2-(S)-(3,4-dicholorophenyl)-4-(N-3,5-bis-trifluoromethylbenzoyl)methylamino)butanal (prepared in step A) following the procedure described in Example 1 step E to give the title compound.

MS (CI) 714 (M$^+$+H) ($^{35}$Cl×2), 716 ($^{35}$Cl, $^{37}$Cl)

EXAMPLE 34

1-(3-((S)-(3,4-Dichlorophenyl))-4-(N-3,5-bis-(trifluoromethyl)benzoyl(methylamino))butyl)-4-(2-(1'-(tetrazolyl)methyl)phenyl)-piperazine The title compound was prepared as following the procedure in Example 33, Step D using 1-t-butoxycarbonyl-4-(2-(1'-(tetrazolyl)methyl)phenyl)-piperazine prepared in Example 33, Step C.

MS (CI) 714 (M$^+$+H) ($^{35}$Cl×2), 716 ($^{35}$Cl, $^{37}$Cl)

EXAMPLE 35

1-(3-((S)-(3,4-Dichlorophenyl))-4-(N-3,5-bis-(trifluoromethyl)benzoyl(methylamino))butyl)-4-(2-(1'-(1',2',4'-triazolyl)methyl)phenyl)-piperazine Step A 1-t-Butoxycarbonyl-4-(2-(1'-(1',2',4'-triazolyl)methyl)phenyl)-piperazine and 1-t-Butoxycarbonyl-4-(2-(4'-(1',2',4'-triazolyl)methyl)phenyl)-piperazine Following the procedure described in Example 33, Step C, the title compounds were prepared using 1,2,4-triazole instead of 1-H tetrazole.

1-t-Butoxycarbonyl-4-(2-(1'-(1',2',4'-triazolyl)methyl)phenyl)-piperazine $^1$H-NMR (500 MHz CDCl$_3$) δ 1.50 (9H, s), 2.81 (4H, s), 3.56 (4H, s), 5.49 (2H, s), 7.1–8.1 (6H, m).
Mass Spectrum (CI) 344 (M$^+$+H).

1-t-Butoxycarbonyl-4-(2-(4'-(1',2',4'-triazolyl)methyl)phenyl)-piperazine $^1$H-NMR (500 MHz CDCl3) δ 1.50 (9H, s), 2.79 (4H, s), 3.56 (4H, s), 5.29 (2H, s), 7.1–7.42 (4H, m), 8.21 (2H, s).
Mass Spectrum (CI) 344 (M$^+$+H).

Step B: 1-(3-((S)-(3,4-Dichlorophenyl))-4-(N-3,5-bis-(trifluoromethyl)benzoyl(methylamino))butyl)-4-(2-(1'-(1',2',4'-triazolyl)methyl)phenyl)-piperazine According to the procedure described in Example 33, Step D, the title compound was prepared from 1-t-butoxycarbonyl-4-(2-(1',2',4'-triazolyl)methyl)phenyl)-piperazine Mass Spectrum (CI) 713 (M$^+$+H, $^{35}$Cl×2), 715 (M$^+$+H, $^{35}$Cl, $^{37}$Cl)

EXAMPLE 36

1-(3-((S)-(3,4-Dichlorophenyl))-4-(N-3,5-bis-(trifluoromethyl)benzoyl(methylamino))butyl)-4-(2-(4'-(1',2',4'-triazolyl)-methyl)-phenyl)-piperazine According to the procedure described in Example 33, Step D, the title compound was prepared from 1-t-butoxycarbonyl-4-(2-(4'-(1',2',4'-triazolyl)methyl)phenyl)-piperazine prepared in Example 35, Step A.

Mass Spectrum (CI) 713 (M$^+$+H, $^{35}$Cl×2), 715 (M$^+$+H, $^{35}$Cl, $^{37}$Cl)

EXAMPLE 37

1-(3-((S)-(3,4-Dichlorophenyl))-4-(N-3,5-bis-(trifluoromethyl)benzoyl(methylamino))butyl)-4-(2-(1'-(1',2',3'-triazolyl)-methyl)phenyl)-piperazine Step A: 1-t-Butoxycarbonyl-4-(2-(1'-(1',2',3'-triazolyl)methyl)phenyl)-piperazine The title compound was prepared according to the procedure described in Example 33, Step C using 1,2,3-triazole istead of 1H-tetrazole.

$^1$H-NMR (400 MHz CDCl3) δ 1.46 (9H, s), 2.78 (4H, s), 3.55 (4H, s), 5.70 (2H, s), 7.05–7,75 (6H, s).

Step B 1-(3-((S)-(3,4-Dichlorophenyl))-4-(N-3,5-bis-(trifluoromethyl)benzoyl(methylamino))butyl)-4-(2-(1'-(1',2',3'-triazolyl)-methyl)-phenyl)-piperazine Following the procedure described in Example 33, Step D, the title compound was prepared using 1-t-butoxycarbonyl-4-(2-((1',2',3'-triazolyl)methyl)phenyl)-piperazine.

MS (CI) 713 (M$^+$+H, $^{35}$Cl×2), 715 (M$^+$+H, $^{35}$Cl, $^{37}$Cl)

EXAMPLE 38

1-(3-((S)-(3,4-Dichlorophenyl))-4-(N-3,5-bis-(trifluoromethyl)benzoyl(methylamino))butyl)-4-(2-(methanesulfonylaminomethyl)phenyl)-piperazine Step A: 1-t-Butoxycarbonyl-4-(2-methanesulfonylaminomethyl)phenyl)-piperazine The piperazine synthesized in Example 1, Step C was subjected to the condition described in Example 1 Step D using methanesulfonyl chloride instead of acetyl chloride.

Step B 1-(3-((S)-(3,4-Dichlorophenyl))-4-(N-3,5-bis-(trifluoromethyl)benzoyl(methylamino))butyl)-4-(2-(methanesulfonylaminomethyl)phenyl)-piperazine The piperazine obtained in Step A was reacted with the aldehyde prepared in Example 33, Step A following the conditions described in Example 1, Step E to give the title compound.

MS (CI) 739 ($M^+$+H)($^{35}$Cl×2), 741 ($M^+$+H)($^{35}$Cl, $^{37}$Cl)

EXAMPLE 39

1-(3-((S)-(4-Chlorophenyl))-4-(N-3,5-bis-(trifluoromethyl)benzoyl(methylamino))butyl)-4-(2-(1'-(tetrazolyl)methyl)-phenyl)-piperazine 1-t-Butoxycarbonyl-4-(2-((1',2',3',4'-tetrazolyl)methyl)phenyl)-piperazine prepared in Example 33, Step C was subjected to the conditions described in Example 9 Step D, then reacted with 4-bromo-2-((S)-(4-Chlorophenyl))-4-((N-3,5-bis-trifluoromethylbenzoyl)methylamino)-butane (prepared in Example 30) according to the procedure described in Example 15 step C to give the title compound.

MS (CI) 680 ($M^+$+H)

The compounds in Examples 40 to 44 were prepared by successively carrying out the procedures described in Example 9, Step D and Example 15, Step C, using the piperazines synthesized in Example 33, Step C for Example 40, Example 35, Step A for Examples 41 and 42, Example 37, Step A for Example 43, and Example 38, Step A for Example 44, which in each case are allowed to react with the bromide prepared in Example 30.

EXAMPLE 40

1-(3-((S)-(4-Chlorophenyl))-4-(N-3,5-bis-(trifluoromethyl)benzoyl(methylamino))butyl)-4-(2-(2'-(tetrazolyl)methyl)phenyl)-piperazine

MS (CI) 680 ($M^+$+H)

EXAMPLE 41

1-(3-((S)-(4-Chlorophenyl))-4-(N-3,5-bis-(trifluoromethyl)benzoyl(methylamino))butyl)-4-(2-(1'-(1',2',4'-triazolyl)methyl)phenyl)-piperazine

MS (CI) 679 ($M^+$+H)

EXAMPLE 42

1-(3-((S)-(4-Chlorophenyl))-4-(N-3,5-bis-trifluoromethylbenzoyl(methylamino))butyl-4-(2-(4'-(1',2',4'-triazolyl)methyl)phenyl)-piperazine

MS (CI) 679 ($M^+$+H)

EXAMPLE 43

1-(3-((S)-(4-Chlorophenyl))-4-(N-3,5-bis-(trifluoromethyl)benzoyl(methylamino))butyl)-4-(2-(1'-(1',2',3'-triazolyl)-methyl)-phenyl)-piperazine

MS (CI) 679 ($M^+$+H)

EXAMPLE 44

1-(3-((S)-(4-Chlorophenyl))-4-(N-3,5-bis-(trifluoromethyl)benzoyl(methylamino))butyl)-4-(2-(methanesulfonylaminomethyl)phenyl)-piperazine

MS (CI) 705 ($M^+$+H)

EXAMPLE 45

1-(3-((S)-(3,4-Dichlorophenyl))-4-(N-3-fluoro-5-(trifluoromethyl)benzoyl(methylamino))butyl)-4-(2-(1'-(tetrazolyl)methyl)phenyl)-piperazine Step A: 3-((S)-(3,4-Dichlorophenyl))-4-((3-fluoro-5-dimethylbenzoyl)methyl-amino)-butanal The title compound was prepared following the procedure described in Example 1, Step A using 3-fluoro-5-trifluoromethylbenzoic acid instead of 3,5-dimethylbenzoic acid.

Step B: 4-Bromo-2-((S)-(3,4-Dichlorophenyl))-4-((N-3-fluoro-5-trifluoromethylbenzoyl)methylamino)-butane The aldehyde prepared in Step A was treated with the conditions described in Example 15, Steps A and B to give the title compound.

Step C: 1-(3-((S)-(3,4-Dichlorophenyl))-4-(N-3-fluoro-5-(trifluoromethyl)benzoyl(methylamino))butyl)-4-(2-(1'-(tetrazolyl)-methyl)phenyl)-piperazine 1-t-Butoxycarbonyl-4-(2-(1'-(tetrazolyl)methyl)phenyl)-piperazine (prepared in Example 33, Step C) was deprotected according to the conditions in Example 9, Step D and the product was carried on according to Example 1, Step E using the aldehyde prepared in Step A above to give the title compound.

MS (CI) 664 ($M^+$+H) ($^{35}$Cl×2), 666 ($M^+$+H) ($^{35}$Cl, $^{37}$Cl)

EXAMPLE 46

1-(3-((S)-(3,4-Dichlorophenyl))-4-(N-3-fluoro-5-trifluoromethyl)benzoyl(methylamino))butyl)-4-(2-(2'-(tetrazolyl)methyl)phenyl)-piperazine 1-t-Butoxycarbonyl-4-(2-(2'-(tetrazolyl)methyl)phenyl)-piperazine (prepared in Example 33, Step C) was subjected to the conditions described in Example 45, Step C to give the title compound.

MS (CI) 664 ($M^+$+H) ($^{35}$Cl×2), 666 ($M^+$+H) ($^{35}$Cl, $^{37}$Cl)

EXAMPLE 47

1-(3-((S)-(3,4-Dichlorophenyl))-4-(N-3-fluoro-5-trifluoromethylbenzoyl(methylamino))butyl)-4-(2-(methanesulfonylaminomethyl)phenyl)-piperazine 1-t-Butoxycarbonyl-4-(2-(methanesulfonylaminomethyl)phenyl)-piperazine prepared in Example 38, Step A was subjected to the conditions described in Example 45, Step C to give the title compound.

MS (CI) 689 (M$^+$+H) ($^{35}$Cl×2), 691 (M$^+$+H) ($^{35}$Cl, $^{37}$Cl)

EXAMPLE 48

1-(3-((S)-(3,4-Dichlorophenyl))-4-((S)-(N-3,5-bis-(trifluoromethyl)benzoyl(methylamino)))-5-hydroxy-pentyl)-4-(2-(1'-tetrazolyl)-methyl)phenyl)-piperazine

Step A: Diazomethyl-(2-(S)-(3,4-dichlorophenyl)-pent-4-enyl)-ketone

To a solution of 2-(S)-(3,4-dichlorophenyl)-pent-4-enoic acid (5.04 g, 20.6 mmol) in 60 mL of dichloromethane was added 2.15 mL (24.6 mmol) of oxalyl chloride and 0.1 mL of dimethylformamide with cooling in an ice-water bath. The cooling bath was then removed and the reaction mixture was stirred at rt overnight. The solvent was removed under reduced pressure, and the resulting material was diluted in ethyl acetate and concentrated in vacuo in order to remove residual HCl. The residual crude acid chloride was dissolved in 70 mL of ether and was slowly added to a 100 mL ether solution of diazomethane (77 mmol). After stirring for 2 hr at rt, the solvent was removed under vacuum. The resulting yellow oil was chromatographed on silica gel column eluting with a gradient of hexane:ethyl acetate=20:1 to 3:1 to give 4.66 g (84%) of diazomethyl-(2-(S)-(3,4-dichlorophenyl)-pent-4-enyl)-ketone.

$^1$H-NMR (CDCl$_3$ 400 MHz): δ 2.44 (app. quint. 1H), 2.82 (app. quint. 1H), 3.43 (br s. 1H), 4.98 & 5.02 (d of AB quart., 2H), 5.16 (br s, 1H), 5.63 (m, 1H), 7.09 (dd, J=2.2 Hz, 8.3 Hz, 1H), 7.34 (d, J=2.2 Hz, 1H), 7.38 (d, J=8.3 Hz, 1H).

Step B: 3-(R)-(3,4-Dichlorophenyl)-hex-4-enoic acid

To a solution of the above diazoketone 4.56 g (17.0 mmol) in 340 mL of tetrahydrofuran was added 170 mL aqueous solution of silver nitrate 3.02 g (17.8 mmol). After stirring at rt overnight, tetrahydrofuran was removed under reduced pressure. The remaining aqueous layer was extracted with two 100 mL portions of dichloromethane. The combined organic phases were washed with brine, dried over anhydrous magnesium sulfate, filtered, and concentrated. The resulting material was purified by silica gel column chromatography. Elution with dichloromethane:methanol=10:1 gave 3.94 g (90%) of 3-(R)-(3,4-dichlorophenyl)-hex-4-eoic acid.

Step C: 3-(3(S)-(3,4-Dichlorophenyl)-2(S)-azido-1-oxo-5-hexenyl)-4(S)-benzyl-2-oxazolidinone A solution of 3-(3(S)-(3,4-dichlorophenyl)-1-oxo-5-hexenyl)-4(S)-benzyl-2-oxazolidinone (190 mg, 0.45 mmol; prepared from 3-(R)-(3,4-dichlorophenyl)-hex-4-enoic acid (from Step B above) and 4(S)-benzyl-2-oxazolidinone according to the procedure of Evans, D. A.; et. al. *J. Am. Chem. Soc.* 1990, 112, 4011–4030) in THF (2.5 mL) was added to a solution of KHMDS (1.0 mL of 0.5M in PhCH$_3$, 0.50 mmol), and THF (1.5 mL) at −78° C. The reaction was maintained at −78° C. for 30 min whereupon a solution of trisyl azide (177 mg, 0.57 mmol) and THF (1.5 mL) was added. The mixture was stirred for 2 min and HOAc (0.13 mL, 4.6 mmoL) was added. The reaction mixture was stirred 1 h in a 30° C. water bath, whereupon it was diluted with H$_2$O (50 mL) and extracted with CH$_2$Cl$_2$ (3×30 mL). The combined organic extracts were washed with sat. aq. NaHCO$_3$, brine, dried (MgSO$_4$) and concentrated in vacuo. The residue was purified by column chromatography (silica gel 60, 15–25% EtOAc/hexanes) to afford the title compound (169 mg, 81%) as a colorless oil.

$^1$H NMR (CDCl$_3$, 500 MHz) δ 7.44 (d, 1H, J=8.2 Hz), 7.20–7.46 (m, 6H), 7.15 (d, 1H, J=8.3 Hz), 5.58–5.65 (m, 1H), 5.45 (d, 1H, J=8.4 Hz), 5.03–5.05 (m, 1H), 4.97–5.02 (m, 1H), 4.64–4.70 (m, 1H), 4.26–4.34 (m, 2H), 3.28–3.36 (m, 2H), 2.88 (dd, 1H, J=9.1, 13.5 Hz), 2.47 (t, 2H, J=7.3 Hz) ppm.

Step D: 2(S)-Azido-3(S)-(3,4-dichlorophenyl)-5-hexen-1-ol

To a solution of 3-(3(S)-(3,4-dichlorophenyl)-2(S)-azido-1-oxo-5-hexenyl)-4(S)-benzyl-2-oxazolidinone (890 mg, 1.94 mmol) and THF (25 mL) at 0° C. was added MeOH (126 mL, 3.1 mmoL), followed by LiBH$_4$ (68 mg, 3.1 mmol). The mixture was allowed to stir for 2 h, and was then quenched by addition of sat. aq. Rochelle salts (50 mL) and was allowed to warm to room temp and stirred vigorously for 2 h. The mixture was diluted with H$_2$O (150 mL) and extracted with CH$_2$Cl$_2$ (3×100 mL). The combined organic extracts were washed with brine, dried (Na$_2$SO$_4$) and concentrated in vacuo. The residue was purified by column chromatography (silica gel 60, 10–40% EtOAc/hexanes) to afford the alcohol (452 mg, 82%) as a colorless oil.

$^1$H NMR (CDCl$_3$, 500 MHz) δ 7.36–7.42 (m, 2H), 7.10 (dd, 1H, J=2.1, 8.2 Hz), 5.59–5.69 (m, 1H), 5.09 (dd, 1H, J=1.4, 17.1 Hz), 5.05 (dd, 1H, J=0.9, 10.3 Hz), 3.77–3.85 (m, 1H), 3.65 (dd, 1H, J=4.5, 11.2 Hz), 3.52 (dd, 1H, J=7.6, 17.3 Hz), 2.88–2.95 (m, 1H), 2.55–2.64 (m, 1H), 2.43–2.52 (m, 1H), 1.28–1.34 (m, 1H) ppm. FTIR 3388, 2930, 2102, 1471, 1271, 1030, 930 cm$^{-1}$.

Step E: 2(S)-Amino-3(S)-(3,4-dichlorophenyl)-5-hexen-1-ol

A solution of 2(S)-azido-3(S)-(3,4-dichlorophenyl)-5-hexen-1-ol (620 mg, 2.17 mmol) and PPh$_3$ (682 mg, 2.60 mmol) in 4:1 THF/H$_2$O (20 mL) was stirred at room temp for 14 h and then heated to 65° C. for 2 h. The reaction mixture was concentrated, and the residue diluted with H$_2$O (50 mL) and extracted with EtOAc (3×50 mL). The combined organic extracts were washed with brine, dried (Na$_2$SO$_4$) and concentrated in vacuo. The residue was purified by column chromatography (silica gel 60, 2.5–8% MeOH/CH$_2$Cl$_2$) to afford the amino alcohol (260 mg, 46%) as a colorless oil.

$^1$H NMR (CDCl$_3$, 500 MHz) δ 7.40 (d, 1H, J=8.3 Hz), 7.25–7.31 (m, 1H), 7.04 (dd, 1H, J=1.9, 8.1 Hz), 5.51–5.61 (m, 1H), 4.92–5.03 (m, 2H), 3.68 (dd, 1H, J=4.1, 10.7 Hz), 3.39 (dd, 1H, J=7.4, 10.6 Hz), 3.01–3.08 (m, 1H), 2.68–2.75 (m, 1H), 2.49–2.56 (m, 1H), 2.32–2.41 (m, 1H) ppm.

Step F: 4(S)-(1(S)-(3,4-Dichlorophenyl)-3-butenyl)-2-oxazolidinone

A solution of 2(S)-amino-3(S)-(3,4-dichlorophenyl)-5-hexen-1-ol (3.85 g, 14.8 mmol) and triphosgene (4.39 g, 14.8 mmol) in THF (100 mL) was stirred at room temp for 2 h. The reaction mixture was concentrated in vacuo and the residue was purified by column chromatography (silica gel 60, 1–5% MeOH/CH$_2$Cl$_2$) to afford the oxazolidone (3.35 g, 79%) as a colorless solid.

$^1$H NMR (CDCl$_3$, 500 MHz) δ 7.45 (d, 1H, J=8.2 Hz), 7.25–7.31 (m, 1H), 7.05 (dd, 1H, J=2.1, 8.3 Hz), 5.50–5.62 (m, 1H), 4.99–5.16 (m, 2H), 4.56 (t, 1H, J=8.7 Hz), 4.21 (dd, 1H, J=6.4, 9.0 Hz), 4.00–4.08 (m, 1H), 2.73–2.80 (m, 1H), 2.30–2.43 (m, 2H) ppm.

Step G: 4(S)-(1(S)-(3,4-Dichlorophenyl)-3-butenyl)-3-methyl-2-oxazolidinone

To a solution of 4(S)-(1(S)-(3,4-Dichlorophenyl)-3-butenyl)-2-oxazolidinone (3.25 g, 11.4 mmol) in DMF (25 mL) at room temp was added NaH (573 mg, 95%, 22.7 mmol). The mixture was stirred for 20 min whereupon MeI (3.54 mL, 57.0 mmol) freshly filtered through basic alumina was added and the resultant reaction mixture was stirred at 70° C. for 14 h. The cooled reaction mixture was diluted with H$_2$O (250 mL) and extracted with EtOAc (3×125 mL). The combined organic extracts were washed with H$_2$O (3×100 mL), brine, dried (Na$_2$SO$_4$) and concentrated in vacuo. The residue was purified by column chromatography (silica gel 60, 1–5% MeOH/CH$_2$Cl$_2$) to afford the title compound (2.93 g, 86%) as a colorless solid and recovered starting material (382 mg, 11%).

$^1$H NMR (CDCl$_3$, 500 MHz) δ 7.45 (d, 1H, J=8.3 Hz), 7.25–7.31 (m, 1H), 7.06 (dd, 1H, J=2.1, 8.2 Hz), 5.52–5.62 (m, 1H), 4.99–5.08 (m, 2H), 4.12–4.26 (m, 2H), 3.82–3.90 (m, 1H), 3.00–3.07 (m, 1H), 2.75 (s, 3H), 2.38–2.49 (m, 2H) ppm.

FTIR 2922, 1747, 1472, 1433, 1405, 1122, 1030, 914, 733 cm$^{-1}$.

Step H: 4(S)-(1(S)-(3,4-Dichlorophenyl)-3-oxopropyl)-3-methyl-2-oxazolidinone The title compound was prepared from 4(S)-(1(S)-(3,4-dichlorophenyl)-3-butenyl)-3-methyl-2-oxazolidinone (prepared in Step G above) as in Example 1, Step A to afford the aldehyde (98%).

$^1$H NMR (CDCl$_3$, 500 MHz) δ 9.76 (s, 1H), 7.45 (d, 1H, J=8.4 Hz), 7.25–7.31 (m, 1H), 7.06 (dd, 1H, J=2.0, 8.5 Hz), 4.15–4.20 (m, 1H), 4.10 (dd, 1H, J=5.5 Hz, 9.2 Hz), 3.88–3.94 (m, 1H), 3.72–3.78 (m, 1H), 2.99 (ddd, 1H, J=0.9, 9.8, 17.8 Hz), 2.84 (s, 3H), 2.79 (dd, 1H, J=4.1, 17.9 Hz) ppm.

Step I: 4(S)-(1(S)-(3,4-Dichlorophenyl)-3-(4-(2-(1'-(tetrazolyl)-methyl)phenyl)-1-piperazinyl)-propyl)-3-methyl-2-oxazolidinone The title compound was prepared (77%) from 4(S)-(1(S)-(3,4-dichlorophenyl)-3-oxopropyl)-3-methyl-2-oxazolidinone (prepared in Step H above) and 1-(2-(1'-(tetrazolyl)-methyl)phenyl)-piperazine (prepared according to the procedure in Example 34) as in Example 1, Step E.

$^1$H NMR (CDCl$_3$, 500 MHz) δ 8.52 (s, 1H), 7.47 (d, 1H, J=8.3 Hz), 7.42 (dt, 1H, J=1.9, 8.1 Hz), 7.15–7.38 (m, 4H), 7.09 (dd, 1H, J=2.1, 8.3 Hz), 5.66 (s, 2H), 4.26 (t, 1H, J=8.9 Hz), 4.17 (dd, 1H, J=6.2, 9.2 Hz), 3.82–3.90 (m, 1H), 3.07–3.14 (m, 1H), 2.80–2.92 (m, 4H), 2.73 (s, 3H), 2.50–2.61 (m, 2H), 2.38–2.50 (m, 2H), 2.20–2.33 (m, 2H), 1.65–1.90 (m, 3H) ppm.

Step J: 2(S)-Amino-3(S)-(3,4-dichlorophenyl)-5-(4-(2-(1'-(tetrazolyl))-methylphenyl)-1-piperazinyl))-pentan-1-ol To a solution of 4(S)-(1(S)-(3,4-dichlorophenyl)-3-(4-(2-(1'-(tetrazolyl)-methyl)phenyl)-1-piperazinyl)-propyl)-3-methyl-2-oxazolidinone (88 mg, 0.166 mmol) and EtOH (2 mL) was added 1M aq KOH (2 mL). The resultant mixture was heated to 85° C. for 14 h. The cooled mixture was then diluted with H$_2$O (50 mL) and extracted with EtOAc (3×50 mL). The combined organic extracts were washed with brine, dried (Na$_2$SO$_4$), and concentrated in vacuo yielding the amino alcohol (77 mg, 92%) as a colorless solid.

$^1$H NMR (CDCl$_3$, 500 MHz) δ 8.52 (s, 1H), 7.08–7.42 (m, 7H), 5.66 (s, 2H), 3.76 (dd, 1H, J=3.7, 11.2 Hz), 3.60 (dd, 1H, J=3.9, 11.2 Hz), 2.80–2.96 (m, 4H), 2.63–2.68 (m, 1H), 2.52–2.62 (m, 2H), 2.40–2.51 (m, 2H), 2.31 (s, 3H), 2.14–2.22 (m, 3H), 2.04–2.14 (m, 2H) ppm.

Step K: 1-(3-((S)-(3,4-Dichlorophenyl))-4-((S)-(N-3,5-bis-(trifluoromethyl)benzoyl(methylamino)))-5-hydroxypentyl)-4-(2-(1'-(tetrazolyl)-methyl)phenyl)-piperazine To a solution of 2(S)-amino-3(S)-(3,4-dichlorophenyl)-5-(4-(2-(1'-(tetrazolyl))-methylphenyl)-1-piperazinyl))-pentan-1-ol (24 mg, 0.048 mmol) and CH$_2$Cl$_2$ (1.5 mL) at 0° C. was added Et$_3$N (13.3 μL, 0.096 mmol), and 3,5-bis(trifluoromethyl)benzoyl chloride (9.0 μL, 0.050 mmol). The resultant reaction mixture was stirred 30 min at 0° C. whereupon it was purified directly, without concentration, by column chromatography (silica gel 60, 2.5–8% MeOH/CH$_2$Cl$_2$) to afford the title compound (26 mg) as a colorless solid.

Mass spectrum (CI): m/z=744 ($^{35}$Cl+$^{35}$Cl isotope+H$^+$), 746 ($^{37}$Cl+$^{35}$Cl isotope+H$^+$).

EXAMPLE 49

1-(3-((S)-(3,4-Dichlorophenyl))-4-((S)-(N-3,5-bis-(trifluoromethyl)benzoyl(methylamino)))-5-hydroxy-pentyl)-4-(2-(1',2',4'-triazolyl)-methylphenyl)-piperazine

Step A: 4(S)-(1(S)-(3,4-Dichlorophenyl)-3-(4-(2-(1'-(1',2',4'-triazolyl)-methyl)phenyl)-1-piperazinyl)-propyl)-3-methyl-2-oxazolidinone The title compound was prepared (98%) from 4(S)-(1(S)-(3,4-dichlorophenyl)-3-oxopropyl)-3-methyl-2-oxazolidinone (prepared in Example 48, Step H) and 1-(2-(1'-(1',2',4'-triazolyl)-methyl)phenyl)-piperazine (prepared according to the procedure in Example 33, Step D) as in Example 1, Step E.

$^1$H NMR (CDCl$_3$, 500 MHz) δ 8.08 (s, 1H), 7.94 (s, 1H), 7.68 (dd, 1H, J=7.1, 12.1 Hz), 7.45–7.60 (m, 2H), 7.32–7.40 (m, 2H), 7.09 (dd, 1H, J=2.1, 8.2 Hz), 5.44 (s, 2H), 4.27 (t, 1H, J=9.0 Hz), 4.17 (dd, 1H, J=6.1, 9.1 Hz), 3.82–3.88 (m, 1H), 3.08–3.16 (m, 1H), 2.82–2.94 (m, 4H), 2.73 (s, 3H), 2.52–2.63 (m, 2H), 2.42–2.51 (m, 2H), 2.20–2.34 (m, 2H), 1.71–1.93 (m, 3H) ppm.

Step B: 2(S)-Amino-3(S)-(3,4-dichlorophenyl)-5-(4-(2-(1'-(1',2',4'-triazolyl))-methylphenyl)-1-piperazinyl))-pentan-1-ol To a solution of 4(S)-(1(S)-(3,4-dichlorophenyl)-3-(4-(2-(1'-(tetrazolyl)-methyl)phenyl)-1-piperazinyl)-propyl)-3-methyl-2-oxazolidinone (78 mg, 0.147 mmol) and EtOH (2 mL) was added 1M aq KOH (2 mL). The resultant mixture was heated to 85° C. for 14 h. The cooled mixture was then diluted with $H_2O$ (50 mL) and extracted with EtOAc (3×50 mL). The combined organic extracts were washed with brine, dried ($Na_2SO_4$), and concentrated in vacuo yielding the amino alcohol (71 mg, 96%) as a colorless solid.

$^1$H NMR (CDCl$_3$, 500 MHz) δ 8.08 (s, 1H), 7.95 (s, 1H), 7.06–7.72 (m, 7H), 5.44 (s, 2H), 3.77 (dd, 1H, J=3.7, 11.5 Hz), 3.60 (dd, 1H, J=3.9, 11.2 Hz), 2.80–2.96 (m, 4H), 2.61–2.67 (m, 1H), 2.53–2.61 (m, 2H), 2.42–2.52 (m, 2H), 2.32 (s, 3H), 2.16–2.27 (m, 3H), 2.07–2.15 (m, 2H) ppm.

Step C: 1-(3-((S)-(3,4-Dichlorophenyl))-4-((S)-(N-3, 5-bis-(trifluoromethyl)benzoyl(methylamino)))-5-hydroxy-pentyl)-4-(2-(1'-(1',2',4'-triazolyl))-methyl)phenyl)-piperazine To a solution of 2(S)-amino-3(S)-(3,4-dichlorophenyl)-5-(4-(2-(1'-(1',2',4'-triazolyl))-methylphenyl)-1-piperazinyl))-pentan-1-ol (22 mg, 0.044 mmol) and CH$_2$Cl$_2$ (1.5 mL) at 0° C. was added Et$_3$N (12.0 μL, 0.088 mmol), and 3,5-bis(trifluoromethyl)benzoyl chloride (8.3 μL, 0.046 mmol). The resultant reaction mixture was stirred 30 min at 0° C. whereupon it was purified directly, without concentration, by column chromatography (silica gel 60, 2.5–8% MeOH/ CH$_2$Cl$_2$) to afford the title compound (20 mg) as a colorless solid.

Mass spectrum (CI): m/z=743 ($^{35}$Cl+$^{35}$Cl isotope+H$^+$), 745 ($^{37}$Cl+$^{35}$Cl isotope+H$^+$).

EXAMPLE 50

1-(3-((S)-(3,4-Dichlorophenyl))-4-(N-3,5-dimethylbenzoyl)(methylamino))butyl)-4-(2-(methylthiomethyl)phenyl)-piperazine Step A: 1-t- Butoxycarbonyl-4-(2-(methylthiomethyl)phenyl)-piperazine Potassium t-butoxide (159 mg, 1,42 mmol) in 15 mL of abs. EtOH was saturated with methyl mercaptan gas. To this mixture was added 1-t-butoxycarbonyl-4-(2-(methanesulfonyloxymethyl)phenyl)-piperazine (0.94 mmol, which was generated according to the procedure described in Step C of Example 9). The resulting mixture was refluxed for 50 min and concentrated. The residue was purified by preparative TLC (20% EtOAc in Hex) to give the title compound (157 mg).

$^1$H NMR (200 MHz, CDCl$_3$) δ 1.47 (s, 9H), 2.05 (s, 3H), 2.87 (t, 4H), 3.55 (t, 4H), 3.80 (s, 2H), 7.08 (m, 2H), 7.20 (dd, 1H), 7.35 (dd, 1H).

Step B: 1-(2-(Methylthiomethyl)phenyl)-piperazine

The title compound was prepared from 1-t-butoxycarbonyl-4-(2-(methylthiomethyl)phenyl)-piperazine (from Step A above) according to the procedure given in Example 9,Step D, and was used below without further purification.

Step C: 1-(3-((S)-(3,4-Dichlorophenyl))-4-(N-3,5-dimethylbenzoyl)-(methylamino))butyl)-4-(2-(methylthiomethyl)phenyl)-piperazine The title compound was prepared from 1-(2-(methylthiomethyl)phenyl)-piperazine (from Step B above) and 3-((S)-(3,4-dichlorophenyl))-4-((3,5-dimethylbenzoyl)-methylamino)-butanal (see Example 1, Step A) according to the procedure given in Example 1, Step E.

$^1$H NMR (400 MHz, CDCl$_3$) δ 2.02 (s, 3H), 2.26 (s, 6H), 3.76 (s, 2H).

Mass Spectrum (CI) m/z. 584, 586 (M$^+$+1, M$^+$+3).

EXAMPLE 51

1-(3-((S)-(3,4-Dichlorophenyl))-4-(N-3,5-bistrifluoromethylbenzoyl)-(methylamino))-butyl)-4-(2-(methylthiomethyl)phenyl)-piperazine The title compound was prepared by analogy to the procedure given in Example 50, Step C, using 3-((S)-(3,4-dichlorophenyl))-4-((3,5-bis(trifluoromethyl)benzoyl)methylamino)-butanal (from Example 33, Step A) instead of 3-((S)-(3,4-dichlorophenyl))-4-((3,5-dimethylbenzoyl)methylamino)-butanal.

$^1$H NMR (400 MHz, CDCl$_3$) δ 2.03 (s, 3H), 3.76 (s, 2H).

Mass Spectrum (CI) m/z 692.1 (M$^+$+1).

EXAMPLE 52

1-(3-((S)-(3,4-Dichlorophenyl))-4-(N-3-methylbenzoyl)-(methylamino))butyl)-4-(2-(methylthiomethyl)phenyl)-piperazine The title compound was prepared by analogy to the procedure given in Example 50, Step C, using 3-((S)-(3,4-dichlorophenyl))-4-((3-methylbenzoyl)methylamino)-butanal instead of 3-((S)-(3,4-dichlorophenyl))-4-((3,5-dimethylbenzoyl)methylamino)-butanal.

$^1$H NMR (400 MHz, CDCl$_3$) δ 2.02 (s, 3H), 2.31 (s, 3H), 3.76 (s, 2H).

Mass Spectrum (CI) m/z 570.3, 572.3 (M$^+$+1, M$^+$+3).

EXAMPLE 53

1-(3-((S)-(3,4-Dichlorophenyl))-4-(N-3,5-dimethylbenzoyl)-(methylamino))butyl)-4-(2-(methylthiomethyl)phenyl)-piperazine, S-oxide The title compound was prepared from 1 equiv. of 1-(3-((S)-(3,4-dichlorophenyl))-4-(N-3,5-dimethylbenzoyl)-(methylamino))butyl)-4-(2-(methylthiomethyl)phenyl)-piperazine (from Example 50, Step C) and 1.5 equiv of oxone (potassium peroxymonosulfate) in MeOH/H$_2$O at 0° C. for 6 min.

$^1$H NMR (400 MHz, CDCl$_3$) δ 2.27 (s, 6H), 2.40 (s, 3H), 4.07 (d, 1H), 4.14 (d, 1H).

Mass Spectrum (CI) m/z 600.2, 602.3 (M$^+$+1, M$^+$+3).

EXAMPLE 54

1-(3-((S)-(3,4-Dichlorophenyl))-4-(N-3,5-bistrifluoromethylbenzoyl)-(methylamino))-butyl)-4-(2-(methylthiomethyl)phenyl)-piperazine, S-oxide The title compound was prepared according to the procedure given in Example 53, using 1-(3-((S)-(3,4-dichlorophenyl))-4-(N-3,5-bistrifluoromethylbenzoyl)-(methylamino))-butyl)-4-(2-(methylthiomethyl)phenyl)-piperazine (from Example 51) as starting material.

$^1$H NMR (400 MHz, CDCl$_3$) δ 2.40 (s, 3H), 4.06 (d, 1H), 4.15 (d, 1H).

Mass Spectrum (CI) m/z 708.1 (M$^+$+1).

EXAMPLE 55

1-(3-((S)-(3,4-Dichlorophenyl))-4-(N-3-methylbenzoyl)-(methylamino))butyl)-4-(2-(methylthiomethyl)phenyl)-piperazine, S-oxide The title compound was prepared according to the procedure given in Example 53, using 1-(3-((S)-(3,4-dichlorophenyl))-4-(N-3-methylbenzoyl)-(methylamino))butyl)-4-(2-(methylthiomethyl)phenyl)-piperazine (from Example 52) as starting material.

$^1$H NMR (400 MHz, CDCl$_3$) δ 2.31 (s, 3H), 2.40 (s, 3H), 4.07 (d, 1H), 4.13 (d, 1H).

Mass Spectrum (CI) m/z 586.2, 588.2 (M$^+$+1, M$^+$+3).

EXAMPLE 56

1-(3-((S)-(3,4-Dichlorophenyl))-4-(N-3,5-dimethylbenzoyl)-(methylamino))butyl)-4-(2-(methylthiomethyl)phenyl)-piperazine, S, S-dioxide The title compound was prepared from 1-(3-((S)-(3,4-dichlorophenyl))-4-(N-3,5-dimethylbenzoyl)-(methylamino))butyl)-4-(2-(methylthiomethyl)phenyl)-piperazine, S-oxide and 3 equiv of oxone in MeOH/H$_2$O at room temperature for 1 h.

$^1$H NMR (400 MHz, CDCl$_3$) δ 2.27 (s, 6H), 2.67 (s, 3H), 4.39 (s, 2H).

Mass Spectrum (CI) m/z 616.2 (M$^+$+1).

EXAMPLE 57

1-(3-((S)-(3,4-Dichlorophenyl))-4-(N-3,5-bistrifluoromethylbenzoyl)-(methylamino))-butyl)-4-(2-(methylthiomethyl)phenyl)-piperazine, S, S-dioxide The title compound was prepared from 1-(3-((S)-(3,4-dichlorophenyl))-4-(N-3,5-bistrifluoromethylbenzoyl)-(methylamino))-butyl)-4-(2-(methylthiomethyl)phenyl)-piperazine, S-oxide and 3 equiv of oxone in MeOH/H$_2$O at room temperature for 1 h.

$^1$H NMR (400 MHz, CDCl$_3$) δ 2.68 (s, 6H), 4.39 (s, 2H).

Mass Spectrum (CI) m/z 724.1 (M$^+$+1).

EXAMPLE 58

1-(3-((S)-(3,4-Dichlorophenyl))-4-(N-3-methylbenzoyl)-(methylamino))butyl)-4-(2-(methylthiomethyl)phenyl)-piperazine, S, S-dioxide The title compound was prepared from 1-(3-((S)-(3,4-Dichlorophenyl))-4-(N-3-methylbenzoyl)-(methylamino))butyl)-4-(2-(methylthiomethyl)phenyl)-piperazine, S-oxide and 3 equiv of oxone in MeOH/H$_2$O at room temperature for 1 h.

$^1$H NMR (400 MHz, CDCl$_3$) δ 2.31 (s, 3H), 2.68 (s, 6H), 4.39 (s, 2H).

Mass Spectrum (CI) m/z 602, 604.3 (M$^+$+1, M$^+$+3).

Additional compounds for Formula I can be prepared from the piperazine starting materials given in the following Examples 59 or Example 60 or from the sources listed below by using the methods given in Example 1, Step E, Example 15, Step C or Example 17:

EXAMPLE 59

7-(1-Piperazinyl)triazolo(2,3-a)pyrimidine dihydrochloride

Step A: 7-(1-(4-t-Butyloxycarbonyl)piperazinyl)triazolo(2,3-a)pyrimidine

7-Chloro-triazolo(2,3-a)pyrimidine (*Chem. Pharm. Bull.*, 1959, 7, 907) (1.01 g, 6.54 mmol), was suspended in isoamyl alcohol (25 mL) and 1-(t-butyloxycarbonyl)piperazine (4.86 g, 26.13 mmol) was added. This solution (dissolution occurred readily upon warming) was heated under reflux, under nitrogen for 1 hr and then the reaction mixture was cooled, evaporated to dryness and the residue was dissolved in CH$_2$Cl$_2$ (100 mL) and 10% aqu. Na$_2$CO$_3$ (100 mL). After shaking, the layers were separated and the organic layer was washed with 10% aqu. Na$_2$CO$_3$ (2×100 mL) and the pooled organic layers were dried (over MgSO$_4$), filtered, and evaporated to dryness. This oily residue was dissolved in a little CH$_2$Cl$_2$, absorbed onto silica gel 60, and applied to a silica gel 60 column (3.5×22.0 cm), packed and developed in CH$_2$Cl$_2$. Fractions containing the required product were pooled and evaporated to dryness to give a white solid which was crystallized from CH$_2$Cl$_2$/Et$_2$O to give 1.47 g of the title compound as a white crystalline solid. Yield 1.71 g (5.63 mmol, 86% yield) in two crops.

Analysis calculated for C$_{14}$H$_{20}$N$_6$O$_2$ (304) C, 55.25; H, 6.62; N, 27.61 Found: C, 55.17; H, 6.32; N, 27.75

Step B: 7-(1-Piperazinyl)triazolo(2,3-a)pyrimidine dihydrochloride 7-(1-(4-t-Butyloxycarbonyl)piperazinyl)triazolo(2,3-a)pyrimidine prepared as described in step A (0.301 g, 0.99 mmol), was dissolved in anhydrous HCO$_2$H (10 mL) and allowed to stand at room temperature for 1½ hr and then was evaporated to dryness in vacuo. This residue was dissolved in a little H$_2$O and applied to a Dowex 1×2 (OH$^-$ form) column (2×23 cm). The column was developed with H$_2$O and fractions containing the required product were pooled and evaporated to dryness to give 0.21 g. TLC indicated a small amount of starting material remaining and the residue was then dissolved in CF$_3$CO$_2$H (10 mL) and allowed to stand at room temperature for 45 min. The reaction was then evaporated to dryness slowly under a nitrogen stream and the residue was evaporated to dryness once from H$_2$O before being dissolved in a little H$_2$O and passed down a Dowex 1×2 (OH$^-$ form) column (2×25 cm) as before. Fractions containing the required product were pooled and evaporated to dryness to give the title compound as a white solid (0.21 g, quantitative yield) in the free base form.

Analysis calculated for C$_9$H$_{12}$N$_6$•1.7 H$_2$O (234.86) C, 46.02; H, 6.61; N, 35.78 Found: C, 46.31; H, 6.01; N, 35.64

A portion of this material (0.10 g) was dissolved in EtOH (3.5 mL) and 3.49M HCl in MeOH (1 mL) was added. A white precipitate formed immediately which was removed by centrifugation after standing at room temperature for 4 hr and was washed with cold EtOH (2×5 mL) and Et$_2$O (5 mL) to give 0.11 g (0.407 mmol) of the title compound as the dihydrochloride salt.

Analysis calculated for C$_9$H$_{14}$N$_6$Cl$_2$.0.7H$_2$O (289.75) C, 37.30; H, 5.36; N, 29.00 Found: C, 37.52; H, 5.17; N, 28.92

EXAMPLE 60

7-(1-Piperazinyl)triazolo(2,3-a)pyrimidine dihydrochloride

Step A: 7-Chloro-triazolo(2,3-a)pyrimidine

This was prepared according to procedures given in *Chem. Pharm. Bull.*, 7, 907 (1959).

Step B: 7-(1-(4-t-Butyloxycarbonyl)piperazinyl)
triazolo(2,3-a)pyrimidine

7-Chloro-triazolo(2,3-a)pyrimidine, prepared as described in Step A above (1.01 g, 6.54 mmol), was suspended in isoamyl alcohol (25 mL) and 1-(t-butyloxycarbonyl)piperazine (4.86 g, 26.13 mmol) was added. This solution (dissolution occurred readily upon warming) was heated under reflux, under nitrogen for 1 hr and then the reaction mixture was cooled, evaporated to dryness and the residue was dissolved in $CH_2Cl_2$ (100 mL) and 10% aq. $Na_2CO_3$ (100 mL). After shaking, the layers were separated and the organic layer was washed with 10% aqu. $Na_2CO_3$ (2×100 mL) and the pooled organic layers were dried (over $MgSO_4$), filtered, and evaporated to dryness. This oily residue was dissolved in a little $CH_2Cl_2$, absorbed onto silica gel 60, and applied to a silica gel 60 column (3.5×22.0 cm), packed and developed in $CH_2Cl_2$. Fractions containing the required product were pooled and evaporated to dryness to give a white solid which was crystallized from $CH_2Cl_2/Et_2O$ to give 1.47 g of the title compound as a white crystalline solid. Yield 1.71 g (5.63 mmol, 86% yield) in two crops.

Anal. Calc. for $C_{14}H_{20}N_6O_2$ (304): C, 55.25; H, 6.62; N, 27.61 Found: C, 55.17; H, 6.32; N, 27.75

Step C: 7-(1-Piperazinyl)triazolo(2,3-a)pyrimidine
dihydrochloride 7-(1-(4-t-Butyloxycarbonyl)piperazinyl)triazolo(2,3-a)pyrimidine, prepared as described in Step B above (0.301 g, 0.99 mmol), was dissolved in anhydrous $HCO_2H$ (10 mL) and allowed to stand at room temperature for 1½ hr and then was evaporated to dryness in vacuo. This residue was dissolved in a little $H_2O$ and applied to a Dowex 1×2 ($OH^-$ form) column (2×23 cm). The column was developed with $H_2O$ and fractions containing the required product were pooled and evaporated to dryness to give 0.21 g. TLC indicated a small amount of starting material remaining and the residue was then dissolved in $CF_3CO_2H$ (10 mL) and allowed to stand at room temperature for 45 min. The reaction was then evaporated to dryness slowly under a nitrogen stream and the residue was evaporated to dryness once from $H_2O$ before being dissolved in a little $H_2O$ and passed down a Dowex 1×2 ($OH^-$ form) column (2×25 cm) as before. Fractions containing the required product were pooled and evaporated to dryness to give the title compound as a white solid (0.21 g, quantitative yield).in the free base form.

Anal. Calc. for $C_9H_{12}N_6 \cdot 1.7H_2O$ (234.86): C, 46.02; H, 6.61; N, 35.78 Found: C, 46.31; H, 6.01; N, 35.64

A portion of this material (0.10 g) was dissolved in EtOH (3.5 mL) and 3.49M HCl in MeOH (1 mL) was added. A white precipitate formed immediately which was removed by centrifugation after standing at room temperature for 4 hr and was washed with cold EtOH (2×5 mL) and $Et_2O$ (5 mL) to give 0.11 g (0.407 mmol) of the title compound as the dihydrochloride salt.

Anal. Calc. for $C_9H_{14}N_6Cl_2 \cdot 0.7H_2O$ (289.75): C, 37.30; H, 5.36; N, 29.00 Found: C, 37.52; H, 5.17; N, 28.92

Additional starting materials are prepared as described in U.S. Pat. No. 5,057,517 which is hereby incorporated by reference:

6-(1-piperazinyl)-8-methylpurine dihydrochloride,
6-(1-piperazinyl)-8,9-dimethylpurine dihydrochloride,
6-(1-piperazinyl)-9-methyl-3-deazapurine dihydrochloride, (i.e. 1-methyl-4-(1-piperazinyl)-1H-imidazo(4,5-c)pyridine dihydrochloride),
8-bromo-6-(1-piperazinyl)purine dihydrochloride,
8-bromo-9-methyl-6-(1-piperazinyl)purine dihydrochloride,
2,9-dimethyl-8-methylamino-6-(1-piperazinyl)purine dihydrochloride,
2,9-dimethyl-8-dimethylamino-6-(1-piperazinyl)purine dihydrochloride,
2,9-dimethyl-6-(1-piperazinyl)-8-(1-pyrrolidinyl)purine dihydrochloride,
8-methoxy-9-methyl-6-(1-piperazinyl)purine dihydrochloride,
9-methyl-6-(1-piperazinyl)-8-(1-pyrrolidinyl)purine dihydrochloride,
8-dimethylamino-9-methyl-6-(1-piperazinyl)purine dihydrochloride,
6-(1-piperazinyl)-2,8,9-trimethylpurine dihydrochloride,
2,8-dimethyl-6-(1-piperazinyl)purine dihydrochloride,
2-chloro-9-methyl-6-(1-piperazinyl)purine dihydrochloride,
9-methyl-2-morpholino-6-(1-piperazinyl)purine dihydrochloride,
9-methyl-6-(1-piperazinyl)-2-(1-pyrrolidinyl)purine dihydrochloride,
9-methyl-2-methylamino-6-(1-piperazinyl)purine dihydrochloride,
2-dimethylamino-9-methyl-6-(1-piperazinyl)purine dihydrochloride,
2,8-bis(dimethylamino)-9-methyl-6-(1-piperazinyl)purine dihydrochloride,
2-methoxy-9-methyl-6-(1-piperazinyl)purine dihydrochloride,
9-methyl-6-(1-piperazinyl)-2-(2-propoxy)purine dihydrochloride,
2-dimethylamino-6-(1-piperazinyl)purine dihydrochloride,
2-amino-6-(1-piperazinyl)purine dihydrochloride,
2-methoxy-6-(1-piperazinyl)-9-(1-propyl)purine dihydrochloride,
2-methylthio-6-(1-piperazinyl)-9-(1-propyl)purine dihydrochloride,
2-ethoxy-9-methoxymethyl-6-(1-piperazinyl)purine maleate,
9-ethoxymethyl-2-methoxy-6-(1-piperazinyl)purine maleate,
9-cyclopropylmethyl-2-ethoxy-6-(1-piperazinyl)purine dihydrochloride,
2-methoxy-9-methoxyethyl-6-(1-piperazinyl)purine dihydrochloride,
2-methoxy-6-(1-piperazinyl)-9-(1-(2-propynyl)purine dihydrochloride,
9-(1-allenyl)-2-methoxy-6-(1-piperazinyl)purine dihydrochloride,
2-methoxy-6-(1-piperazinyl)-9-(1-(2-propenyl))purine dihydrochloride,
9-cyclopropyl-2-ethyl-6-(1-piperazinyl)purine,
2-ethyl-9-(1-(2,2,2-trifluoroethylamino))-6-(1-piperazinyl)purine,
2-ethyl-9-methyl-6-(1-piperazinyl)purine dihydrochloride,
2-methoxy-6-(1-piperazinyl)-9-(2-propyl)purine dihydrochloride,
2-methoxy-9-(1-(2-oxopropyl))-6-(1-piperazinyl)purine dihydrochloride,
9-(1-(2,2-difluoropropyl))-2-methoxy-6-(1-piperazinyl)purine,
2-ethyl-9-(2-fluoroethyl)-6-(1-piperazinyl)purine dihydrochloride,
2-methoxy-6-(1-piperazinyl)-9-(2-furanylmethyl)purine,
9-((1S,2R)-2-fluoro-1-methylpropyl)-2-methoxy-6-(1-piperazinyl)purine,
9-((1R,2S)-2-fluoro-1-methylpropyl)-2-methoxy-6-(1-piperazinyl)purine,
9-((1S,2S)-2-fluoro-1-methylpropyl)-2-methoxy-6-(1-piperazinyl)purine,
9-((1R,2R)-2-fluoro-1-methylpropyl)-2-methoxy-6-(1-piperazinyl)purine.

Additional starting materials are prepared as described in U.S. Pat. No. 4,980,350 which is hereby incorporated by reference:

4-methyl-2-(1-piperazinyl)pyrimidine dihydrochloride,
4,5-dimethyl-2-(1-piperazinyl)pyrimidine dihydrochloride,
4,6-dimethyl-2-(1-piperazinyl)pyrimidine dihydrochloride,
4,5,6-trimethyl-2-(1-piperazinyl)pyrimidine dihydrochloride,
6-(1-butyl)-4-methyl-2-(1-piperazinyl)pyrimidine dihydrochloride,
4-(2-butyl)-2-(1-piperazinyl)pyrimidine dihydrochloride,
4-methyl-5-methoxy-4-(1-piperazinyl)pyrimidine dihydrochloride,
2-methyl-4-(1-piperazinyl)-S-triazine dihydrochloride.

Additional starting materials are prepared as described in U.S. Pat. No. 4,876,256 which is hereby incorporated by reference:

6-methyl-2-(1-piperazinyl)pyridine dihydrochloride,
2-(1-piperazinyl)pyridine dihydrochloride.

Additional staring materials are prepared as described in *J. Heterocyclic Chem.*, 27, 1559 (1990) which is hereby incorporated by reference:

8,9-dihydro-1-methyl-5-(1-piperazinyl)-7H-thiopyrano(2,3-e)(1,2,4)triazolo(4,3-a)pyrimidine,
8,9-dihydro-5-(1-piperazinyl)-7H-thiopyrano(2,3-e)(1,2,4)triazolo(4,3-a)pyrimidine,
8,9-dihydro-5-(1-piperazinyl)-7H-tetrazolo(1,5-a)thiopyrano(2,3-e)pyrimidine,
5,6-dihydro-7H-9-(1-piperazinyl)thiopyrano(3,2-d)(1,2,4)triazol(2,3-a)pyrimidine.

What is claimed is:

1. A compound of Formula I

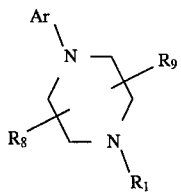

or a pharmaceutically acceptable salt thereof, wherein the nitrogen attached to $R_1$ shown above is optionally quaternized with $C_{1-4}$alkyl or phenyl$C_{1-4}$alkyl or is optionally present as the N-oxide ($N^+O^-$), and wherein:

$R_1$ is selected from a group consisting of:
linear or branched $C_{1-8}$ alkyl, linear or branched $C_{2-8}$ alkenyl, wherein the $C_{1-8}$ alkyl or $C_{2-8}$ alkenyl is optionally mono, di, tri or tetra substituted, the substituents independently selected from:
(a) hydroxy,
(b) oxo,
(c) cyano,
(d) halogen which is defined to include Br, Cl, I, and F,
(e) trifluoromethyl,
(f) phenyl or mono, di or tri-substituted phenyl, the substituents independently selected from
(1) phenyl,
(2) hydroxy,
(3) $C_{1-3}$alkyl,
(4) cyano,
(5) halogen,
(6) trifluoromethyl,
(7) —$NR_6COR_7$,
(8) —$NR_6CO_2R_7$,
(9) —$NR_6CONHR_7$,
(10) —$NR_6S(O)_jR_7$, wherein j is 1 or 2,
(11) —$CONR_6R_7$,
(12) —$COR_6$,
(13) —$CO_2R_6$,
(14) —$OR_6$,
(15) —$S(O)_kR_6$ wherein k is 0, 1 or 2,
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$,
(p) —$S(O)_kR_6$,
(q) heteroaryl, wherein heteroaryl is selected from the group consisting of:
(1) benzimidazolyl,
(2) benzofuranyl,
(3) benzoxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl,
(21) triazolyl,
wherein the heteroaryl is unsubstituted or mono di or tri-substituted, the substituents independently selected from:
(a) phenyl,
(b) hydroxy,
(c) oxo,
(d) cyano,
(e) halogen,
(f) trifluoromethyl;

Ar is selected from the group consisting of

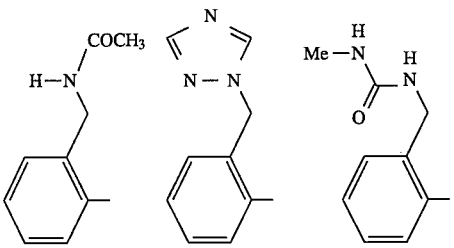

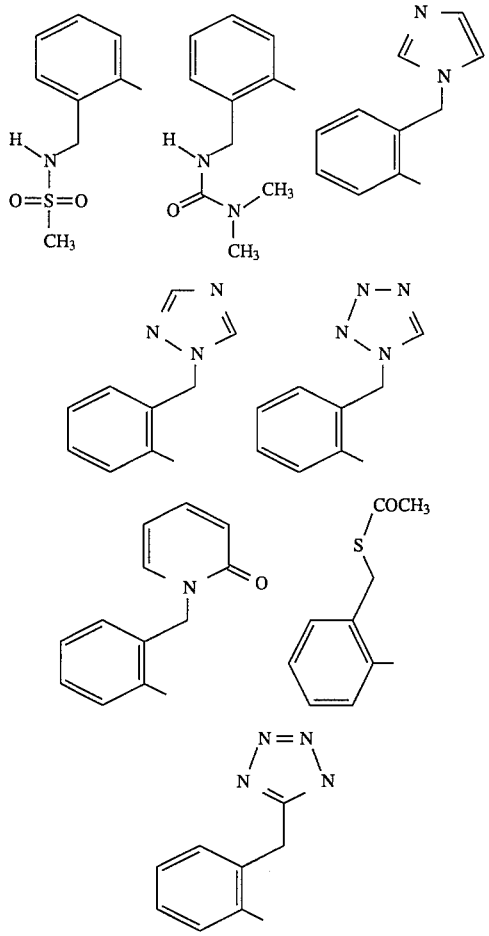

R₆ is
(1) hydrogen,
(2) $C_{1-6}$ alkyl, or mono or di-substituted $C_{1-6}$ alkyl, the substituents independently selected from:
 (a) phenyl,
 (b) hydroxy,
 (c) oxo,
 (d) cyano,
 (e) halogen,
 (f) trifluoromethyl,
(3) phenyl or mono di or tri-substituted phenyl, the substituents independently selected from:
 (a) hydroxy,
 (b) $C_{1-3}$alkyl,
 (c) cyano,
 (d) halogen,
 (e) trifluoromethyl, R₇ is
(1) hydrogen,
(2) $C_{1-6}$ alkyl, or mono or di-substituted $C_{1-6}$ alkyl, the substituents independently selected from:
 (a) phenyl unsubstituted or substituted with
  (1) hydroxy,
  (2) $C_{1-3}$alkyl,
  (3) cyano,
  (4) halogen,
  (5) trifluoromethyl,
  (6) $C_{1-3}$alkyloxy,
 (b) hydroxy,
 (c) oxo,
 (d) cyano,
 (e) halogen,
 (f) trifluoromethyl,
(3) phenyl or mono di or tri-substituted phenyl, the substituents independently selected from:
 (a) hydroxy,
 (b) $C_{1-3}$alkyl,
 (c) cyano,
 (d) halogen,
 (e) trifluoromethyl,
(4) naphthyl or mono di or tri-substituted naphthyl, the substituents independently selected from:
 (a) hydroxy,
 (b) $C_{1-3}$alkyl,
 (c) cyano,
 (d) halogen,
 (e) trifluoromethyl,
(5) $C_{1-3}$alkyloxy,
or R₆ and R₇ are joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
(1) hydroxy,
(2) oxo,
(3) cyano,
(4) halogen,
(5) trifluoromethyl, R₈ and R₉ are each independently hydrogen or substituted $C_{1-4}$alkyl wherein the substitutent is selected from the group consisting of
(1) hydroxy,
(2) hydrogen,
(3) cyano,
(4) halogen,
(5) trifluoromethyl,
(6) $C_{1-3}$alkyloxy.

2. A compound according to claim 1 wherein:
R₁ is selected from a group consisting of:
 $C_3$, $C_4$, $C_5$, $C_6$, $C_7$ or $C_8$ linear or branched alkyl, unsubstituted or mono, di or tri-substituted, the substituents independently selected from:
 (a) hydroxy,
 (b) Cl or F,
 (c) trifluoromethyl,
 (d) phenyl or di-substituted phenyl, the substituents independently selected from:
  (1) phenyl,
  (2) hydroxy,
  (3) $C_{1-3}$alkyl,
  (4) cyano,
  (5) halogen,
  (6) trifluoromethyl,
  (7) —NR₆COR₇,
  (8) —NR₆CO₂R₇,
  (9) —NR₆CONHR₇,
  (10) —NR₆S(O)ⱼR₇, wherein j is 1 or 2,
  (11) —CONR₆R₇,
  (12) —COR₆,
  (13) —CO₂R₆,
  (14) —OR₆,
  (15) —S(O)ₖR₆,
 (e) —NR₆COR₇,
 (f) —NR₆CO₂R₇,
 (g) —NR₆CONHR₇,
 (h) —NHS(O)ⱼR₆,
 (i) —COR₆,
 (j) —OR₆, (k) heteroaryl, wherein heteroaryl is selected from the group consisting of:
   (1) pyrazinyl,
   (2) pyrazolyl,
   (3) pyridyl,
   (4) pyrimidyl, and
   (5) thienyl,
   wherein the heteroaryl is unsubstituted or mono di or tri-substituted, the substituents independently selected from:
      (a) phenyl,
      (b) hydroxy,
      (c) oxo,
      (d) cyano,
      (e) halogen, and
      (f) trifluoromethyl, $R_6$ is selected from:
   (1) hydrogen,
   (2) $C_{1-6}$ alkyl, or mono or di-substituted $C_{1-6}$ alkyl, the substituents independently selected from:
      (a) phenyl,
      (b) hydroxy,
      (c) oxo,
      (d) cyano,
      (e) halogen,
      (f) trifluoromethyl,
   (3) phenyl or mono di or tri-substituted phenyl, the substituents independently selected from:
      (a) hydroxy,
      (b) $C_{1-3}$alkyl,
      (c) cyano,
      (d) halogen,
      (e) trifluoromethyl;

$R_7$ is selected from:
   (1) hydrogen,
   (2) $C_{1-6}$ alkyl, or mono or di-substituted $C_{1-6}$ alkyl, the substituents independently selected from:
      (a) phenyl,
      (b) hydroxy,
      (c) oxo,
      (d) cyano,
      (e) halogen,
      (f) trifluoromethyl,
   (3) phenyl naphthyl or mono di or tri-substituted phenyl, or naphthyl the substituents independently selected from:
      (a) hydroxy,
      (b) $C_{1-3}$alkyl,
      (c) cyano,
      (d) halogen,
      (e) trifluoromethyl, or
   (4) $C_{1-3}$alkyloxy,
   or $R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or di-substituted, the substituents independently selected from:
   (1) hydroxy,
   (2) oxo,
   (3) cyano,
   (4) halogen, or
   (5) trifluoromethyl;

$R_8$ and $R_9$ are each independently hydrogen or substituted $C_{1-4}$alkyl wherein the substitutent is selected from the group consisting of
   (1) hydroxy,
   (2) hydrogen,
   (3) halogen.

3. A compound according to claim 2 wherein:
$R_1$ is selected from a group consisting of:
   $C_4$, $C_5$, $C_6$, $C_7$ or $C_8$ linear or branched alkyl, unsubstituted or mono, di or tri-substituted, the substituents independently selected from:
   (a) hydroxy,
   (b) Cl or F,
   (c) phenyl or mono, di or tri-substituted phenyl, the substituents independently selected from:
      (1) phenyl,
      (2) hydroxy,
      (3) $C_{1-3}$alkyl,
      (4) cyano,
      (5) halogen,
      (6) trifluoromethyl,
   (d) —$NR_6COR_7$, wherein $R_6$ is hydrogen or $C_{1-3}$ alkyl and $R_7$ is phenyl optionally substituted with Cl, F, $CF_3$ or $C_{1-3}$alkyl,
   (e) —$NHS(O)_rR_6$,
   (f) —$COR_6$,
   (h) —$OR_6$,
   and
$R_9$ is hydrogen.

4. A compound according to claim 3 wherein:
$R_1$ is selected from a group consisting of:
   $C_4$, $C_5$, $C_6$, $C_7$ or $C_8$ linear or branched alkyl, mono, di- or tri-substituted, the substituents independently selected from:
   (a) hydroxy,
   (b) Cl or F,
   (c) phenyl or mono or di-substituted phenyl, the substituents independently selected from:
      (1) hydroxy,
      (2) methyl or ethyl,
      (3) Cl or F,
      (4) trifluoromethyl,
   (d) —$NR_6COR_7$, wherein $R_6$ is methyl and $R_7$ is phenyl optionally substituted with halo, $CF_3$, $C_{1-3}$alkyl or $C_{1-3}$alkoxy.

5. A according of Formula I

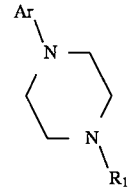

or a pharmaceutically acceptable salt thereof, wherein:
$R_1$ is

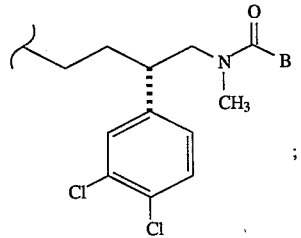

where B is
(a) phenyl or mono di or tri-substituted phenyl wherein the substituents are independently chloro, methyl, phenyl, $C_{1-3}$alkoxy, or $CF_3$;
(b) —$CH_2$phenyl or mono or di-substituted —$CH_2$phenyl wherein the substituents are independently chloro, methyl, phenyl, $C_{1-3}$alkoxy or $CF_3$;

(c) pyridyl or mono di or tri-substituted pyridyl wherein the substituents are independently chloro, methyl, phenyl, $C_{1-3}$alkoxy or $CF_3$; and (d) thiophene or mono or disubstituted thiophene wherein the substituents are independently chloro, methyl, phenyl, $C_{1-3}$alkoxy or $CF_3$; and Ar is unsubstituted or mono substituted phenyl wherein the substituent is selected from the group consisting of:
(a) —$CH_2$-tetrazolyl,
(b) —$CH_2$-triazolyl,
(c) —$CH_2$-imidazolyl,
(d) —$CH_2$—N(H)C(O)N($CH_3$)$_2$,
(e) —$CH_2$—N(H)C(O)N(H)$CH_3$,
(f) —$CH_2$—N(H)C(O)$CH_3$, and
(g) —$CH_2$—N(H)S(O)$_2$$CH_3$,
(h) —$CH_2$-pyridyl,
(i) —$CH_2$-oxopyridyl,
(j) —$CH_2$—O-pyridyl,
(k) mono or di-substituted purinyl wherein the substituents are selected from:
(1) $C_{1-3}$alkyl,
(2) $C_{1-3}$alkoxy,
(3) fluoro,
(4) hydrogen, and
(5) fluoro$C_{1-3}$alkyl.

6. A compound of the formula

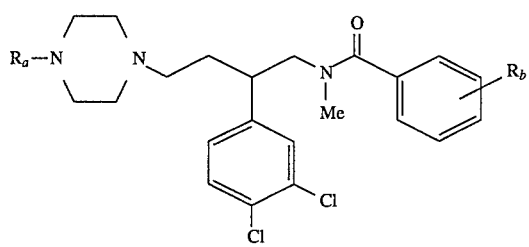

wherein

| $R_a$ | $R_b$ |
|---|---|
| H<br>—NCOCH$_3$<br>(benzyl) | 3,5-diMe |
|  | 3,5-diCl |
|  | 3,5-diCF$_3$ |
| (N-methyl-triazolyl-benzyl) | 3,5-diMe |
|  | 3,5-diCl |
|  | 3,5-diCF$_3$ |
| H H<br>—N⟶NMe<br>O<br>(benzyl ureido) | 3,5-diMe |
|  | 3,5-diCl |
|  | 3,5-diCF$_3$ |

-continued

| $R_a$ | $R_b$ |
|---|---|
| H<br>—N—SO$_2$Me<br>(benzyl) | 3,5-diMe |
|  | 3,5-diCl |
|  | 3,5-diCF$_3$ |
| H<br>—N⟶NMe$_2$<br>O<br>(benzyl ureido) | 3,5-diMe |
|  | 3,5-diCl |
|  | 3,5-diCF$_3$ |
| (imidazolyl-benzyl) | 3,5-diMe |
|  | 3,5-diCF$_3$ |
| (tetrazolyl-benzyl) | 3,5-diMe |
|  | 3,5-diCF$_3$ |

7. A compound selected from the group consisting of
(a) 1-(3-((S)-(3,4-Dichlorophenyl))-4-(N-3,5-dimethylbenzoyl(methylamino))butyl)-4-((2-acetylaminomethyl)-phenyl)-piperazine;
(b) 1-(3-((S)-(3,4-Dichlorophenyl))-4-(N-3,5-dichlorobenzoyl(methylamino))butyl)-4-(2-acetylaminomethylphenyl)-piperazine;
(c) 1-(3-((S)-(3,4-Dichlorophenyl))-4-(N-3,5-dimethylbenzoyl(methylamino))butyl)-4-((2-methylaminocarbonylamino-methyl)phenyl)-piperazine;
(d) 1-(3-((S)-(3,4-Dichlorophenyl))-4-(N-3,5-dimethylbenzoyl(methylamino))butyl)-4-((2-dimethylaminocarbonylamino-methyl)phenyl)-piperazine;
(e) 1-(3-((S)-(3,4-Dichlorophenyl))-4-(N-3,5-dimethylbenzoyl(methylamino))butyl)-4-(2-methylsulfonylaminomethyl-phenyl)-piperazine;
(f) 1-(3-((S)-(3,4-Dichlorophenyl))-4-(N-3,5-dichlorobenzoyl(methylamino))butyl)-4-((2-methylaminocarbonylamino-methyl)phenyl)-piperazine;
(g) 1-(3-((S)-(3,4-Dichlorophenyl))-4-(N-3,5-dichlorobenzoyl(methylamino))butyl)-4-((2-dimethylaminocarbonylamino-methyl)phenyl)-piperazine;
(h) 1-(3-((S)-(3,4-Dichlorophenyl))-4-(N-3,5-dichlorobenzoyl(methylamino))butyl)-4-(2-methylsulfonylaminomethyl-phenyl)-piperazine;
(i) 1-(3-((S)-(3,4-Dichlorophenyl))-4-(N-3,5-dimethylbenzoyl(methylamino))butyl)-4-(2-((1'-imidazolyl)methyl)phenyl)-piperazine;
(j) 1-(3-((S)-(3,4-Dichlorophenyl))-4-(N-3,5-dichlorobenzoyl(methylamino))butyl)-4-(2-(1'-(1',2',4'-triazolyl)methyl-phenyl)-piperazine;
(k) 1-(3-((S)-(3,4-Dichlorophenyl))-4-(N-3,5-dimethylbenzoyl(methylamino))butyl)-4-(2-(1'-(1',2',4'-triazolyl)methyl-phenyl)-piperazine;

(l) 1-(3-((S)-(3,4-Dichlorophenyl))-4-(N-3,5-dimethyl-benzoyl(methylamino))butyl)-4-(2-(1'-(1',2',3',4'-tetrazolyl)methyl-phenyl)-piperazine;

(m) 1-(3-((S)-(3,4-Dichlorophenyl))-4-(N-3,5-dimethyl-benzoyl(methylamino))butyl)-4-(2-(3'-pyridyloxy)methylphenyl)-piperazine; and (n) 1-(3-((S)-(3,4-Dichlorophenyl))-4-(N-3,5-dimethyl-benzoyl(methylamino))butyl)-4-(2-(1'-(2'(1'H)-pyridone)methyl-phenyl)-piperazine.

8. A pharmaceutical composition for antagonizing the effect of substance P in a patient in need of such treatment comprising a pharmaceutically acceptable carrier and a non-toxic therapeutically effective amount of the compound of claim 1.

9. A pharmaceutical composition for the antagonizing the effect of neurokinin A, in a patient in need of such treatment comprising a pharmaceutically acceptable carrier and a non-toxic therapeutically effective amount of the compound of claim 1.

10. A pharmaceutical composition for treating respiratory disease, in a patient in need of such treatment comprising a pharmaceutically acceptable carrier, a non-toxic therapeutically effective amount of the compound of claim 1 and a non-toxic therapeutically effective amount of compound selected from the group consisting of a leukotriene antagonist and a β2 agonist.

11. A method of treating respiratory disease in a patient in need of such treatment which comprises the administration to the patient of a non-toxic therapeutically effective amount of the compound according to claim 1 and optionally a non-toxic therapeutically effective amount of compound selected from the group consisting of a leukotriene antagonist and a β2 agonist.

12. A compound selected from the group consisting of

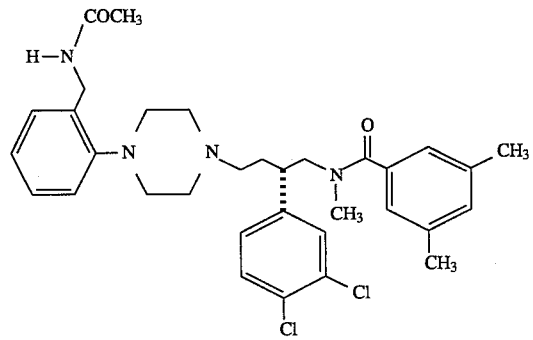

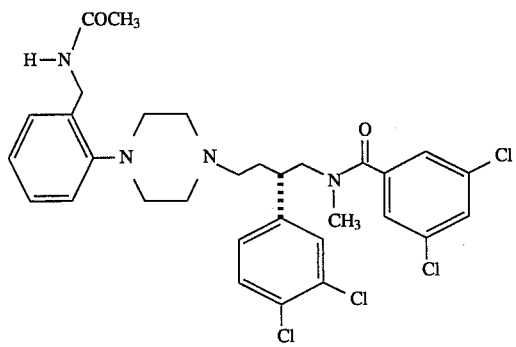

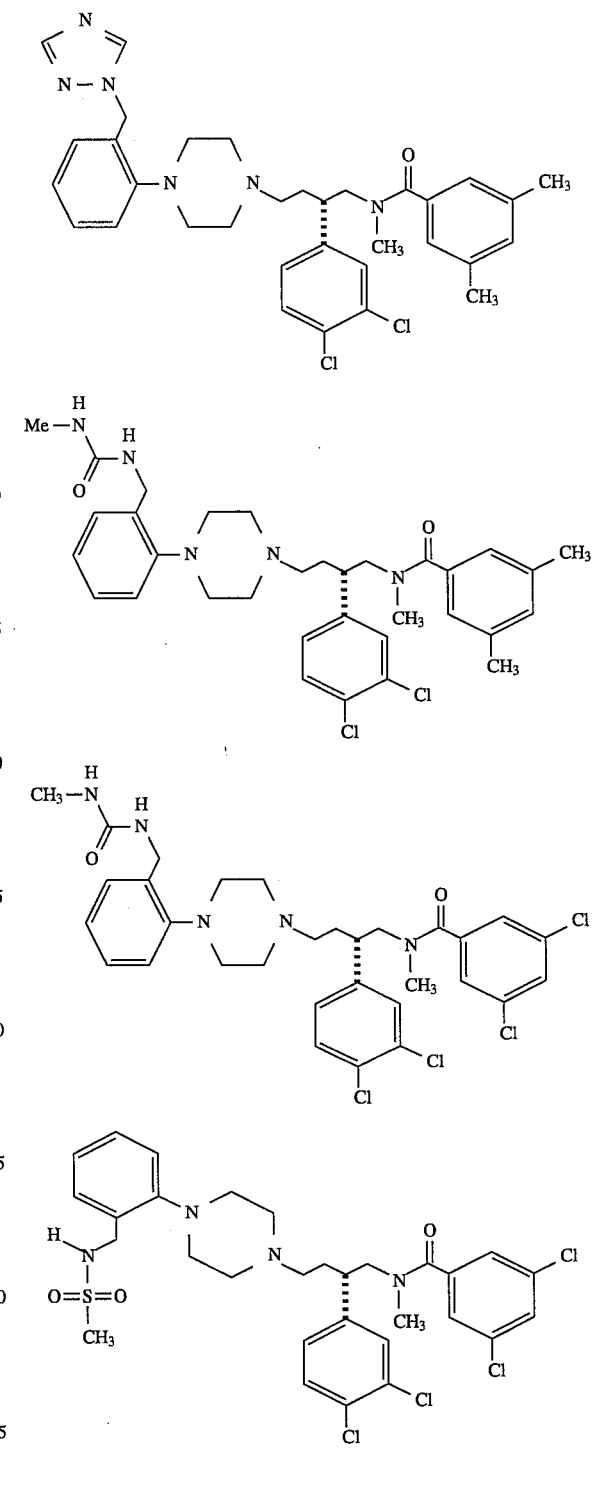

5,607,936
71
-continued
72
-continued
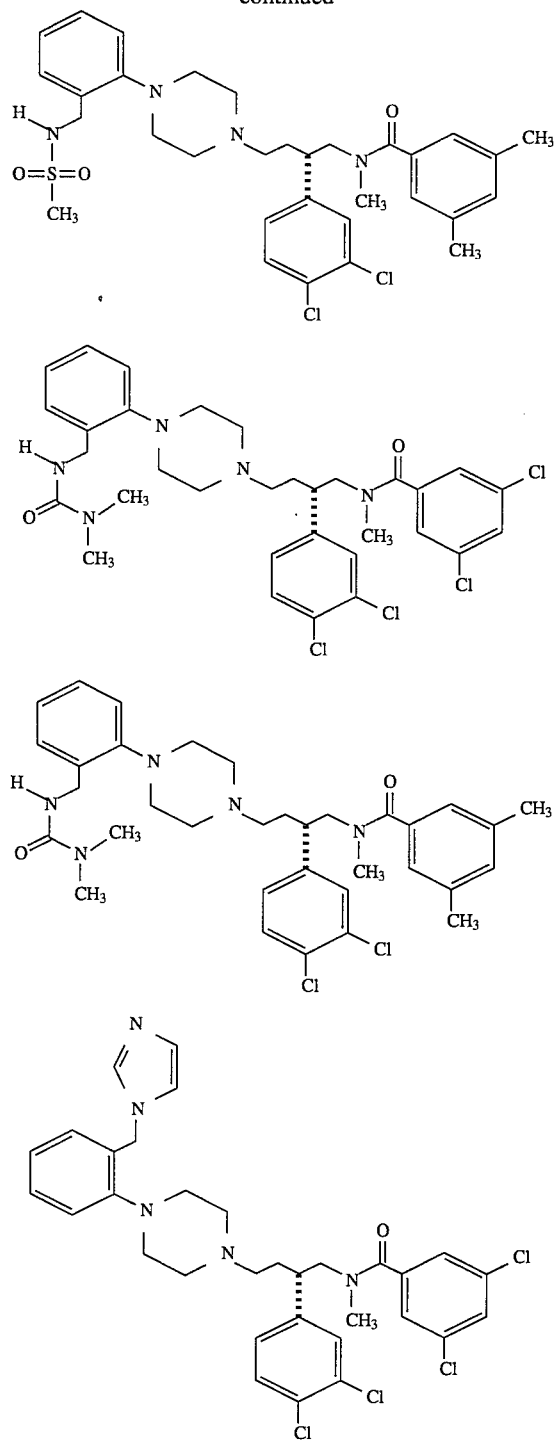
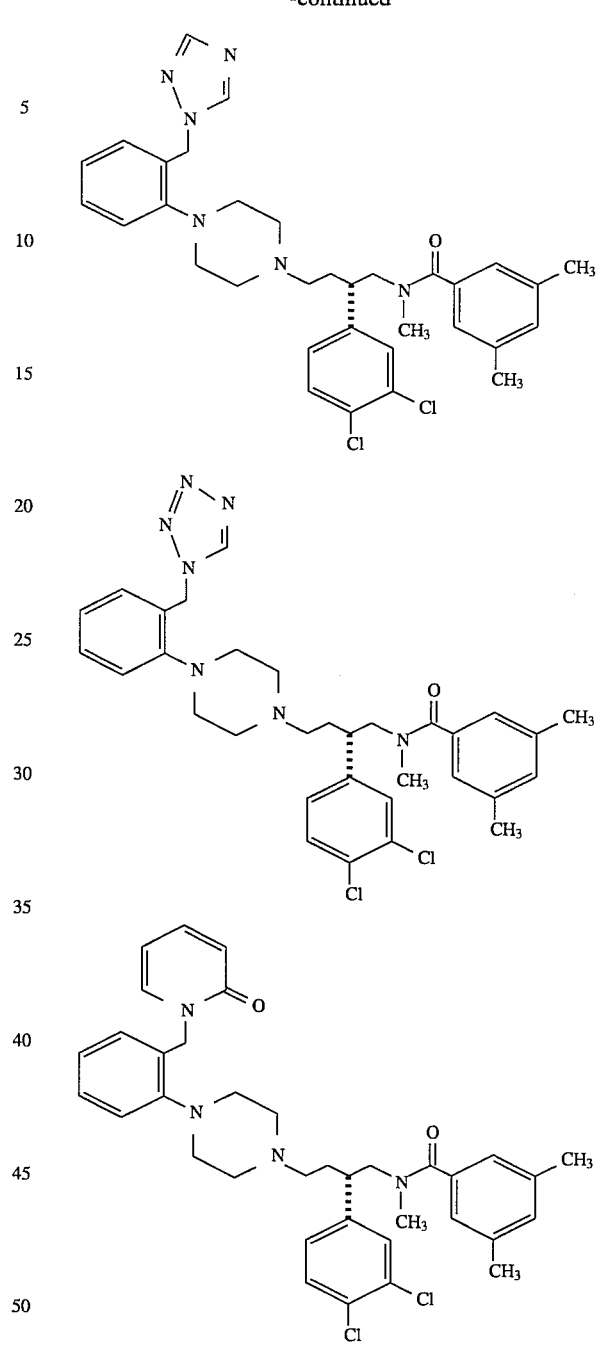

73
-continued
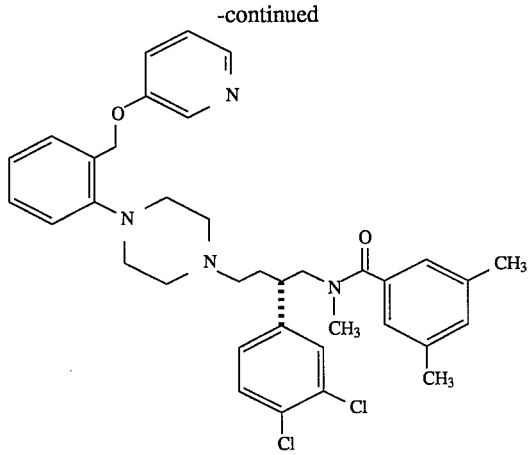
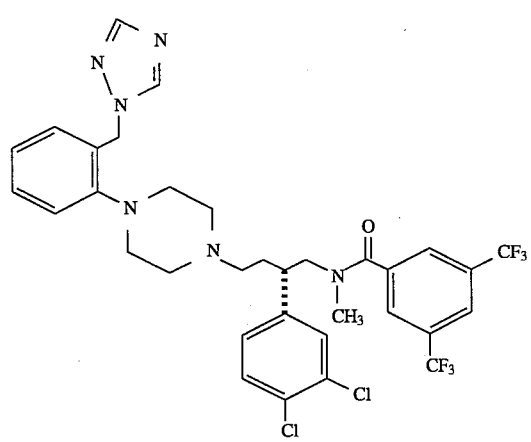
74
-continued
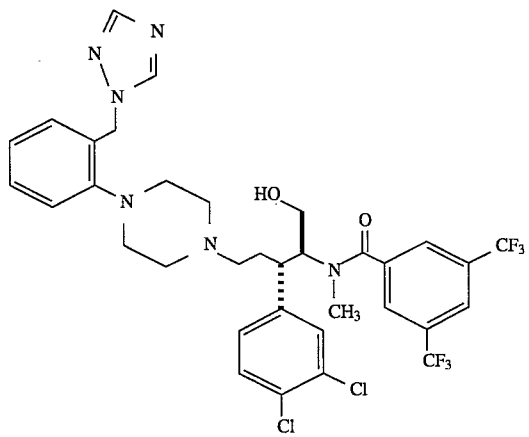
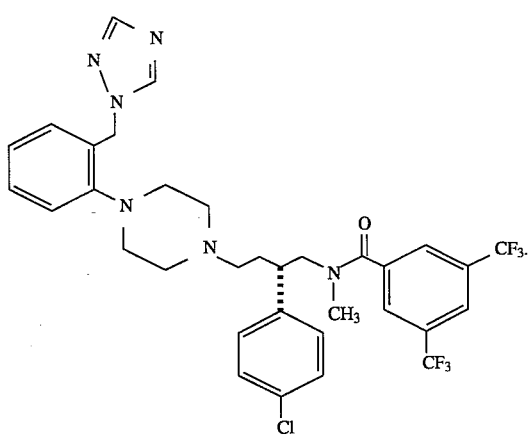
* * * * *